(12) United States Patent
Godfrey et al.

(10) Patent No.: US 10,791,742 B2
(45) Date of Patent: Oct. 6, 2020

(54) PLANT GROWTH REGULATOR COMPOUNDS

(71) Applicant: SYNGENTA PARTICIPATIONS AG, Basel (CH)

(72) Inventors: Christopher Richard Ayles Godfrey, Stein (CH); Mathilde Denise Lachia, Stein (CH); Sebastian Volker Wendeborn, Stein (CH); Davide Sabbadin, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 85 days.

(21) Appl. No.: 16/315,597

(22) PCT Filed: Jun. 28, 2017

(86) PCT No.: PCT/EP2017/065938
§ 371 (c)(1),
(2) Date: Jan. 4, 2019

(87) PCT Pub. No.: WO2018/007217
PCT Pub. Date: Jan. 11, 2018

(65) Prior Publication Data
US 2019/0373893 A1 Dec. 12, 2019

(30) Foreign Application Priority Data
Jul. 5, 2016 (GB) .................................. 1611717.8

(51) Int. Cl.
*A01N 43/86* (2006.01)
*C07D 265/18* (2006.01)
*C07D 413/12* (2006.01)

(52) U.S. Cl.
CPC ........... *A01N 43/86* (2013.01); *C07D 265/18* (2013.01); *C07D 413/12* (2013.01)

(58) Field of Classification Search
None
See application file for complete search history.

(56) References Cited

FOREIGN PATENT DOCUMENTS

| WO | 2016/022910 A2 | 2/2016 |
| WO | 2016128317 A1 | 8/2016 |

OTHER PUBLICATIONS

International Search Report for International Patent Application No. PCT/EP2017/065938 dated Aug. 30, 2017.

*Primary Examiner* — Alton N Pryor
(74) *Attorney, Agent, or Firm* — Baker & Hostetler, LLP; Toni-Junell Herbert

(57) ABSTRACT

The present invention relates to novel sulfonamide derivatives, to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

21 Claims, No Drawings

PLANT GROWTH REGULATOR COMPOUNDS

CROSS-REFERENCE TO RELATED APPLICATIONS

This application is a 371 National Stage application of International Application No. PCT/EP2017/065938, filed Jun. 28, 2017, which claims priority to Great Britain Application No. 1611717.8 filed Jul. 5, 2016, the entire contents of which applications are hereby incorporated by reference.

The present invention relates to novel sulfonamide derivatives, to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

Abscisic acid (ABA) is a plant hormone that plays a major role in plant growth, development and response to abiotic stress. ABA causes many of its cellular responses by binding to a soluble family of receptors called PYR/PYL proteins, which contain a ligand-binding pocket for ABA and other agonists. Direct application of ABA to plants has been shown to improve their water use efficiency. However, ABA is difficult and expensive to prepare and is unstable to environmental conditions and therefor unsuitable for large scale agricultural applications. It is therefore desirable to search for ABA agonists that may be useful for improving plant tolerance to environmental stress such as drought, inhibiting seed germination, regulating plant growth and improving crop yield.

WO2013/148339 reported a new ABA agonist, quinabactin, which binds to the PYR/PRL receptor proteins and causes an abscisic acid response in vivo. Quinabactin has been shown to induce stomatal closure, suppress water loss and promote drought tolerance.

There is a need to identify improved agonists of abscisic acid for improving plant growth and development, and plant tolerance to environmental stresses. The present invention relates to novel analogs of quinabactin that have improved properties. Benefits of the compounds of the present invention include enhanced tolerance to abiotic stress, improved inhibition of seed germination, better regulation of crop growth, improved crop yield, and/or improved physical properties resulting in better plant uptake, water solubility, chemical stability or physical stability.

According to the present invention, there is provided a compound of Formula (I)

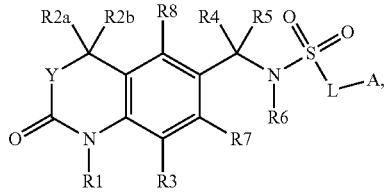

(I)

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$ alkenyl, $C_3$-$C_7$ alkynyl, aryl-$C_1$-$C_7$alkyl, (3-6 membered heterocyclyl)-$C_1$-$C_7$alkyl, phenyl, $C_3$-$C_5$ cycloalkyl and a 4-6 membered heterocyclyl, each optionally substituted with one to three Rx;
R2a and R2b are independently selected from the group consisting of hydrogen, $C_1$-$C_4$ alkyl and $C_1$-$C_4$ haloalkyl; or R2a and R2b, together with the atom to which they are attached, are joined to form a $C_3$-$C_6$ cycloalkyl;
R3, R7 and R8 are independently selected from the group consisting of hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl; or R4 and R5, together with the atom to which they are attached, are joined to form a $C_3$-$C_4$ cycloalkyl or $C_4$ heterocyclyl;
R6 is selected from the group consisting of hydrogen, $C_1$-$C_4$ alkyl, $C_3$-$C_4$ alkenyl, $C_3$-$C_4$ alkynyl, and $C_1$-$C_3$ alkoxy-$C_1$-$C_4$-alkyl;
L is selected from the group consisting of a bond, a linear —$C_1$-$C_4$— alkyl chain, a linear —$C_2$-$C_4$— alkenyl chain, a linear —$C_2$-$C_4$— alkynyl chain, a linear —$C_1$-$C_4$— alkoxy chain whereby the oxygen atom is attached to A, a linear -amino-$C_1$-$C_4$-alkyl- chain whereby the nitrogen atom is attached to A, and a linear $C_1$-$C_2$alkyl-oxy-$C_1$-$C_2$alkyl chain, each optionally substituted with one to three halogen, cyano, $C_1$-$C_4$ alkyl, $C_1$-$C_4$ haloalkyl or $C_1$-$C_4$ alkoxy;
A is selected from the group consisting of hydrogen, $C_1$-$C_7$ alkyl, $C_3$-$C_5$ cycloalkyl, 3-10 membered heterocyclyl and aryl, each optionally substituted with one to three Ry;
Y is selected from the group consisting of O and NRw;
Rw is selected from the group consisting of hydrogen, $C_1$-$C_4$ alkyl, $C_1$-$C_4$ alkoxy, $C_1$-$C_4$ alkoxycarbonyl, $C_1$-$C_4$ haloalkyl, $C_3$-$C_4$ alkenyl, and $C_3$-$C_4$ alkynyl;
Each Rx is, independently of the other, selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;
Each Ry is, independently of the other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl which cycloalkyl is unsubstituted or substituted by one or more Rz; and
Each Rz is, independently of the other, selected from the group consisting of halogen, $C_1$-$C_4$-alkyl and $C_1$-$C_4$-haloalkyl;
wherein A is not butyl when either R4 or R5 is methyl;
and wherein R1 is not methyl when R2a, R2b, R3, R4, R5, R6, R7 and R8 are each hydrogen;
or salts or N-oxides thereof.

The compounds of the present invention may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of the present invention.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups include $C_1$-$C_6$ alkyl, $C_1$-$C_4$ alkyl, and $C_1$-$C_3$ alkyl.

The term "alkenyl", as used herein, is an alkyl moiety having at least one carbon-carbon double bond, for example $C_2$-$C_6$ alkenyl. Specific examples include vinyl and allyl. The alkenyl moiety may be part of a larger group (such as alkenoxy, alkenoxycarbonyl, alkenylcarbonyl, alkyenlaminocarbonyl, dialkenylaminocarbonyl).

The term "acetoxy" refers to —OC(=O)CH$_3$.

The term "alkynyl", as used herein, is an alkyl moiety having at least one carbon-carbon triple bond, for example $C_2$-$C_6$ alkynyl. Specific examples include ethynyl and propargyl. The alkynyl moiety may be part of a larger group (such as alkynoxy, alkynoxycarbonyl, alkynylcarbonyl, alkynylaminocarbonyl, dialkynylaminocarbonyl).

Halogen is fluorine (F), chlorine (Cl), bromine (Br) or iodine (I).

Haloalkyl groups (either alone or as part of a larger group, such as haloalkoxy or haloalkylthio) are alkyl groups which are substituted with one or more of the same or different halogen atoms and are, for example, —CF$_3$, —CF$_2$Cl, —CH$_2$CF$_3$ or —CH$_2$CHF$_2$.

Hydroxyalkyl groups are alkyl groups which are substituted with one or more hydroxyl group and are, for example, —CH$_2$OH, —CH$_2$CH$_2$OH or —CH(OH)CH$_3$.

Alkoxyalkyl groups are an alkoxy group bonded to an alkyl (R—O—R'), for example —(CH$_2$)$_r$O(CH$_2$)$_s$CH$_3$, wherein r is 1 to 6 and s is 1 to 5.

In the context of the present specification the term "aryl" refers to a ring system which may be mono-, bi- or tricyclic. Examples of such rings include phenyl, naphthalenyl, anthracenyl, indenyl or phenanthrenyl.

Unless otherwise indicated, alkenyl and alkynyl, on their own or as part of another substituent, may be straight or branched chain and may contain 2 to 6 carbon atoms, and where appropriate, may be in either the (E)- or (Z)-configuration. Examples include vinyl, allyl, ethynyl and propargyl.

Unless otherwise indicated, cycloalkyl may be mono- or bi-cyclic, may be optionally substituted by one or more $C_1$-$C_6$ alkyl groups, and contain 3 to 7 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" refers to a ring system containing from one to four heteroatoms selected from N, O and S, wherein the nitrogen and sulphur atoms are optionally oxidized, and the nitrogen atom(s) are optionally quaternized. Heterocyclyl includes heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl. In addition, the term "heterocyclyl" includes heterocycloalkyl, a non-aromatic monocyclic or polycyclic ring comprising carbon and hydrogen atoms and at least one heteroatom selected from nitrogen, oxygen, and sulfur such as oxetanyl or thietanyl. A monocyclic heterocycloalkyl may contain 3 to 7 members.

The term "heteroaryl" refers to an aromatic ring system containing from one to four heteroatoms selected from N, O, and S, wherein the nitrogen and sulfur atoms are optionally oxidized, for example having 5, 6, 9 or 10 members, and consisting either of a single ring or of two or more fused rings. Single rings may contain up to three heteroatoms, and bicyclic systems up to four heteroatoms, which will preferably b'e chosen from nitrogen, oxygen and sulfur. Examples of such groups include pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl.

Preferred values of R1, R2a, R2b, R3, R4, R5, R6, R7, R8, L, A, Y, Rw, Rx, Ry and Rz are, in any combination, as set out below.

Preferably R1 is selected from the group consisting of $C_1$-$C_6$ alkyl, $C_1$-$C_6$ haloalkyl, $C_3$-$C_5$ cycloalkyl-$C_1$-$C_6$ alkyl, $C_3$-$C_6$ alkenyl, $C_3$-$C_6$ alkynyl, phenyl and a 4-6 membered heterocyclyl, each optionally substituted with one to three Rx.

Preferably R1 is selected from the group consisting of $C_1$-$C_6$ alkyl, $C_1$-$C_6$ haloalkyl, $C_3$-$C_6$ alkenyl and $C_3$-$C_5$-cycloalkyl-$C_1$-$C_6$ alkyl, each optionally substituted with one to three Rx. Preferably R1 is selected from the group consisting of $C_1$-$C_6$ alkyl, $C_3$-$C_5$ alkenyl, $C_3$-$C_5$-cycloalkyl-$C_1$-$C_2$ alkyl, $C_1$-$C_4$-alkoxy-ethyl and $C_2$-$C_4$ haloalkyl. Preferably, R1 is ethyl, isopropyl, n-propyl, allyl, cyclopropylmethyl, methoxy-ethyl, 2,2,2-trifluoro-ethyl, 2,2-difluoroethyl or 3-fluoro-propyl. The alkyl chain may be branched or linear. In one embodiment R1 is methyl. In one embodiment R1 is ethyl. In one embodiment R1 is n-propyl or iso-propyl. In one embodiment R1 is n-butyl, iso-butyl, sec-butyl or tert-butyl. In one embodiment R1 is allyl, cyclopropylmethyl, 2,2,2-trifluoro-ethyl, 2,2-difluoro-ethyl or 3-fluoropropyl. In one embodiment R1 is 3-fluoro-propyl or n-propyl.

Preferably R2a and R2b are independently selected from the group consisting of hydrogen and $C_1$-$C_4$ alkyl. Preferably R2a and R2b are independently selected from the group consisting of hydrogen and methyl. In one embodiment, R2a is hydrogen. In one embodiment, R2a is methyl. In one embodiment, R2a is methyl and R2b is hydrogen.

Preferably R3 is selected from the group consisting of hydrogen, halogen, cyano, $C_1$-$C_4$ alkyl and $C_1$-$C_4$ alkoxy. Preferably R3 is selected from the group consisting of hydrogen, halogen and $C_4$ alkyl. In one embodiment, R3 is methyl. In one embodiment, R3 is fluoro.

Preferably each of R4 and R5 are independently selected from the group consisting of hydrogen and $C_1$-$C_4$ alkyl. Preferably each of R4 and R5 is independently hydrogen or methyl.

Preferably R6 is hydrogen.

Preferably each of R7 and R8 are independently selected from the group consisting of hydrogen, halogen, cyano, $C_1$-$C_4$ alkyl and $C_1$-$C_4$ alkoxy.

Preferably L is selected from the group consisting of a bond, a linear —$C_1$-$C_4$— alkyl chain, a linear —$C_2$-$C_4$— alkenyl chain, and a linear —$C_2$-$C_4$— alkynyl chain. In one embodiment, L is a bond. In one embodiment, L is a linear —$C_1$-$C_4$— alkyl chain. In one embodiment, L is a —$C_2$-$C_4$— alkenyl chain.

Preferably A is selected from the group consisting of $C_1$-$C_7$ alkyl, phenyl and 3-6 membered heteroaryl, each optionally substituted with one to three Ry. Preferably A is a 5-6 membered heteroaryl or phenyl, each optionally substituted with one to three Ry. Preferably A is phenyl optionally substituted with one to three substituents independently selected from the group consisting of halogen, cyano, $C_1$-$C_4$ alkyl, $C_1$-$C_4$ haloalkyl, $C_1$-$C_4$ haloalkoxy, $C_1$-$C_4$ haloalkylsulfanyl and $C_3$-$C_4$ cycloalkyl. In one embodiment, A is phenyl optionally substituted with one to three substituents independently selected from the group consisting of halogen, $C_1$-$C_4$ alkyl, $C_1$-$C_4$ haloalkyl and $C_1$-$C_4$ haloalkoxy. In one embodiment, A is phenyl. In one embodiment, A is a 5-6 membered heteroaryl selected from the group consisting of pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl. In one embodiment, A is thienyl optionally substituted with one to three substituents independently selected from the group consisting of halogen, $C_1$-$C_4$ alkyl, $C_1$-$C_4$ haloalkyl and $C_1$-$C_4$ haloalkoxy.

In one embodiment, Y is O. In another embodiment, Y is NRw.

Preferably Rw is selected from the group consisting of hydrogen, $C_1$-$C_4$ alkyl and $C_1$-$C_4$ alkoxy. In one embodiment, Rw is selected from the group consisting of hydrogen, methyl, ethyl and methoxy. In a further embodiment, Rw is hydrogen or methyl.

Preferably Rx is selected from the group consisting of halogen, $C_1$-$C_4$ alkyl, $C_1$-$C_4$ haloalkyl and $C_1$-$C_4$ alkoxy. Preferably Rx is selected from the group consisting of halogen and $C_1$-$C_4$ alkyl. In one embodiment, Rx is halogen. In a further embodiment, Rx is methyl. In a further embodiment, Rx is ethyl. In a further embodiment, Rx is methoxy.

Preferably Ry is selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkoxy, $C_1$-$C_4$ haloalkylsulfanyl and $C_3$-$C_4$ cycloalkyl. Preferably, Ry is selected from the group consisting of halogen, $C_1$-$C_4$ haloalkyl and $C_1$-$C_4$ alkyl. In one embodiment, Ry is selected from the group consisting of cyano, methyl, ethyl, cyclopropyl, trifluoromethyl, difluoromethyl, trifluoromethyloxy, difluoromethyloxy and trifluoromethylsulfanyl. In one embodiment, each Ry is selected from the group consisting of halogen, cyano, methyl, ethyl, propyl, cyclopropyl and butyl. In a further embodiment, each Ry is selected from the group consisting of F, Cl, and Br. In one embodiment, Ry is fluoro. In another embodiment, Ry is difluoromethyl. In another embodiment, Ry is trifluoromethyl. In another embodiment, Ry is $C_1$-$C_4$ haloalkylsulfanyl.

Preferably Rz is selected from the group consisting of halogen and $C_1$-$C_4$-alkyl. In one embodiment, Rz is halogen.

In one embodiment of formula (I), R2a is methyl, and R2b, R3, R4, R5, R6, R7 and R8 are hydrogen.

In one embodiment of formula (I):
R1 is selected from the group consisting of $C_1$-$C_6$ alkyl, $C_3$-$C_5$-cycloalkyl-$C_1$-$C_6$ alkyl, $C_3$-$C_6$ alkenyl, $C_1$-$C_3$ alkoxy-$C_1$-$C_6$ alkyl and $C_1$-$C_6$ haloalkyl;
R2a and R2b are independently selected from the group consisting of hydrogen and $C_1$-$C_4$ alkyl;
R3, R7 and R8 are each independently selected from the group consisting of hydrogen, halogen, cyano, $C_1$-$C_4$ alkyl, and $C_1$-$C_4$ alkoxy;
R4 and R5 are each independently selected from the group consisting of hydrogen and $C_1$-$C_4$ alkyl;
R6 is hydrogen;
Y is O;
L is selected from the group consisting of a bond, a linear —$C_1$-$C_4$— alkyl chain, a linear —$C_2$-$C_4$— alkenyl chain, and a linear —$C_2$-$C_4$— alkynyl chain;
A is a 3-10 membered heterocyclyl or aryl, each optionally substituted with one to three Ry; and
Ry is selected from the group consisting of cyano, halogen, $C_1$-$C_4$ alkyl and $C_1$-$C_4$ haloalkyl.

In a further embodiment of formula (I):
R1 is selected from the group consisting of $C_1$-$C_6$ alkyl, $C_3$-$C_5$-cycloalkyl-$C_1$-$C_6$ alkyl and $C_1$-$C_6$ haloalkyl;
R2a is methyl;
R2b, R3, R6, R7 and R8 are hydrogen;
R4 and R5 are each independently selected from the group consisting of hydrogen and $C_1$-$C_4$ alkyl;
Y is O;
L is selected from the group consisting of a bond, a linear —$C_1$-$C_4$— alkyl chain, a linear —$C_2$-$C_4$— alkenyl chain, and a linear —$C_2$-$C_4$— alkynyl chain;
A is a 3-10 membered heterocyclyl or aryl, each optionally substituted with one to three Ry; and
Ry is selected from the group consisting of cyano, halogen, $C_1$-$C_4$ alkyl, and $C_1$-$C_4$ haloalkyl.

In a further embodiment of formula (I):
R1 is selected from the group consisting of $C_1$-$C_6$ alkyl, $C_3$-$C_5$-cycloalkyl-$C_1$-$C_6$ alkyl and $C_1$-$C_6$ haloalkyl;
R2a, R2b, R3, R6, R7 and R8 are hydrogen;
R4 and R5 are each independently selected from the group consisting of hydrogen and $C_1$-$C_4$ alkyl;
Y is O;
L is selected from the group consisting of a bond, a linear —$C_1$-$C_4$— alkyl chain, a linear —$C_2$-$C_4$— alkenyl chain, and a linear —$C_2$-$C_4$— alkynyl chain;
A is a 3-10 membered heterocyclyl or aryl, each optionally substituted with one to three Ry; and
Ry is selected from the group consisting of cyano, halogen, $C_1$-$C_4$ alkyl, and $C_1$-$C_4$ haloalkyl.

In one embodiment of the present invention there is provided a compound of formula (II)

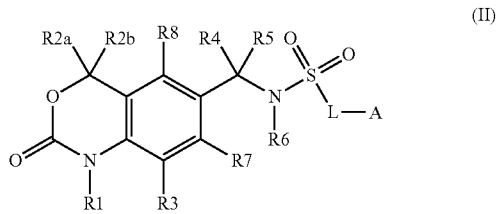

wherein the substituents are as defined above; or salts or N-oxides thereof. Preferred values of R1, R2a, R2b, R3, R4, R5, R6, R7, R8, L, A, Rx, Ry and Rz for compounds of formula (II) are, in any combination, as set out above.

In a further embodiment of the present invention there is provided a compound of formula (III)

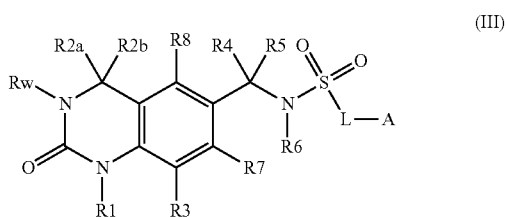

wherein the substituents are as defined above; or salts or N-oxides thereof. Preferred values of R1, R2a, R2b, R3, R4, R5, R6, R7, R8, L, A, Rw, Rx, Ry and Rz for compounds of formula (III) are, in any combination, as set out above.

In another embodiment of the present invention there is provided a compound of formula (IV)

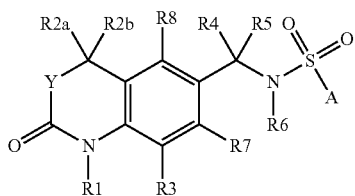

(IV)

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$ alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;
R2a, and R2b are independently selected from the group consisting of hydrogen, $C_1$-$C_4$ alkyl and $C_1$-$C_4$ haloalkyl; or R2a and R2b, together with the atom to which they are attached, are joined to form a $C_3$-$C_6$ cycloalkyl;
R3, R7 and R8 are independently selected from the group consisting of hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl; or R4 and R5, together with the atom to which they are attached, are joined to form a $C_3$-$C_4$ cycloalkyl or $C_3$-$C_4$ heterocyclyl;
R6 is selected from the group consisting of hydrogen, $C_1$-$C_4$ alkyl, $C_3$-$C_4$ alkenyl, $C_3$-$C_4$ alkynyl, and $C_1$-$C_3$ alkoxy-$C_1$-$C_4$-alkyl;
A is selected from the group consisting of hydrogen, $C_1$-$C_7$ alkyl, $C_3$-$C_5$ cycloalkyl, 3-10 membered heterocyclyl and aryl, each optionally substituted with one to three Ry;
Y is selected from the group consisting of O and NRw;
Rw is selected from the group consisting of hydrogen, $C_1$-$C_4$ alkyl, $C_1$-$C_4$ alkoxy, $C_1$-$C_4$ haloalkyl, $C_3$-$C_4$ alkenyl, and $C_3$-$C_4$ alkynyl;
Each Rx is, independently of the other, selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;
Each Ry is, independently of the other, selected from the group consisting of halogen, cyano, $C_1$-$C_4$ alkyl, $C_1$-$C_4$ alkoxy, $C_1$-$C_4$ haloalkyl, $C_1$-$C_4$ haloalkyloxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl which cycloalkyl is unsubstituted or substituted by one or more Rz; and
Each Rz is, independently of the other, selected from the group consisting of halogen, $C_1$-$C_4$-alkyl and $C_1$-$C_4$-haloalkyl;
wherein A is not butyl when either R4 or R5 is methyl;
and wherein R1 is not methyl when R2, R3, R4, R5, R6, R7 and R8 are each hydrogen;
or salts or N-oxides thereof.

In a further embodiment of the present invention there is provided a compound of formula (IV) as described above, wherein R2a is methyl and R2b is hydrogen.

Preferred values of R1, R2a, R2b, R3, R4, R5, R6, R7, R8, A, Y, Rw, Rx, Ry and Rz for compounds of formula (IV) are, in any combination, as set out above.

Table 1 below includes examples of compounds of the present invention.

TABLE 1

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

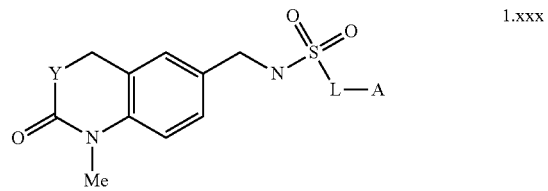

1.xxx

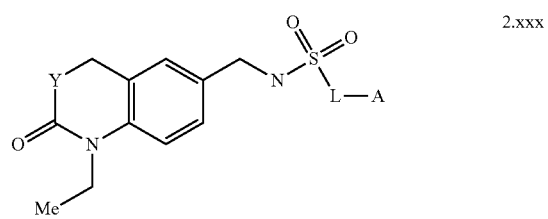

2.xxx

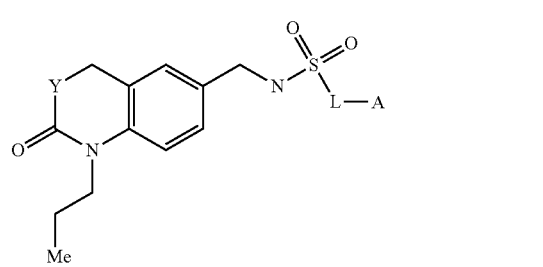

3.xxx

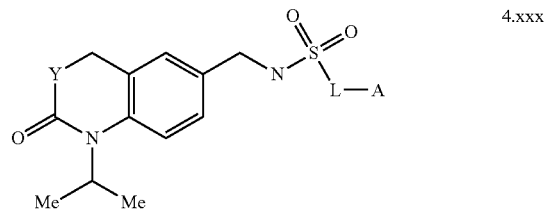

4.xxx

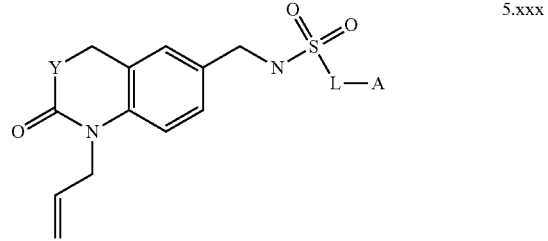

5.xxx

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

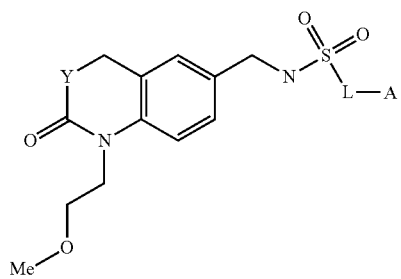
6.xxx

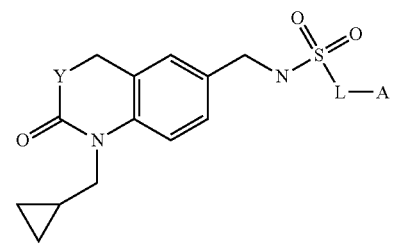
7.xxx

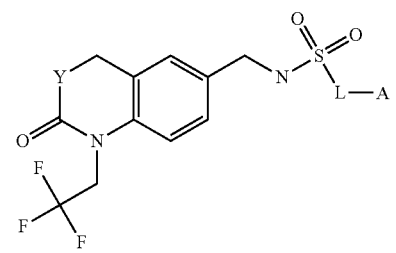
8.xxx

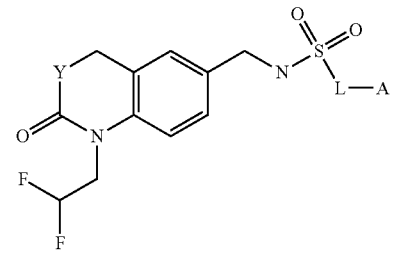
9.xxx

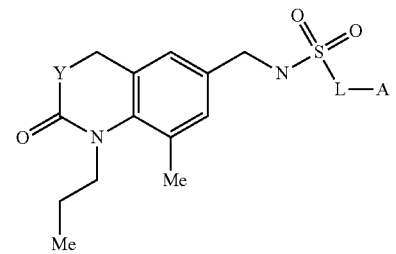
10.xxx

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

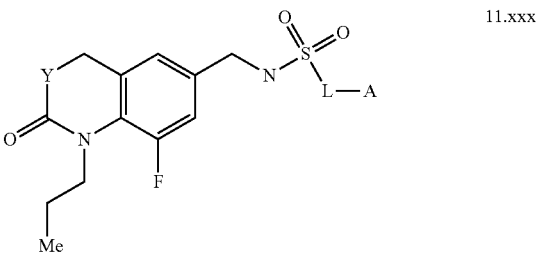
11.xxx

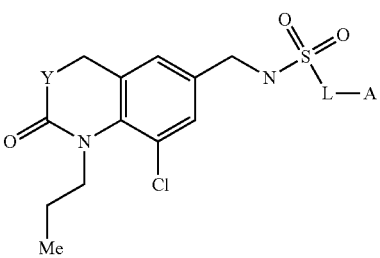
12.xxx

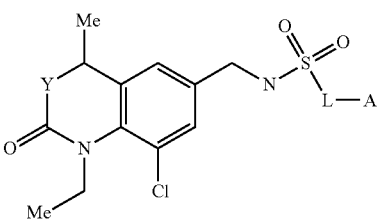
13.xxx

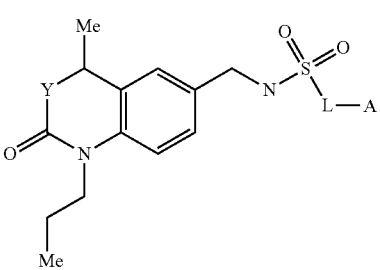
14.xxx

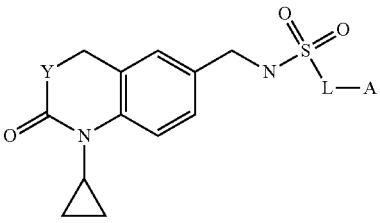
15.xxx

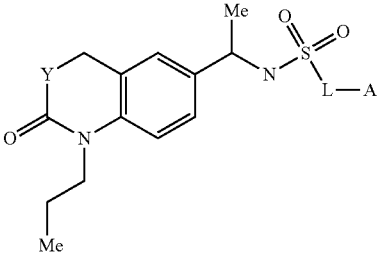
16.xxx

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

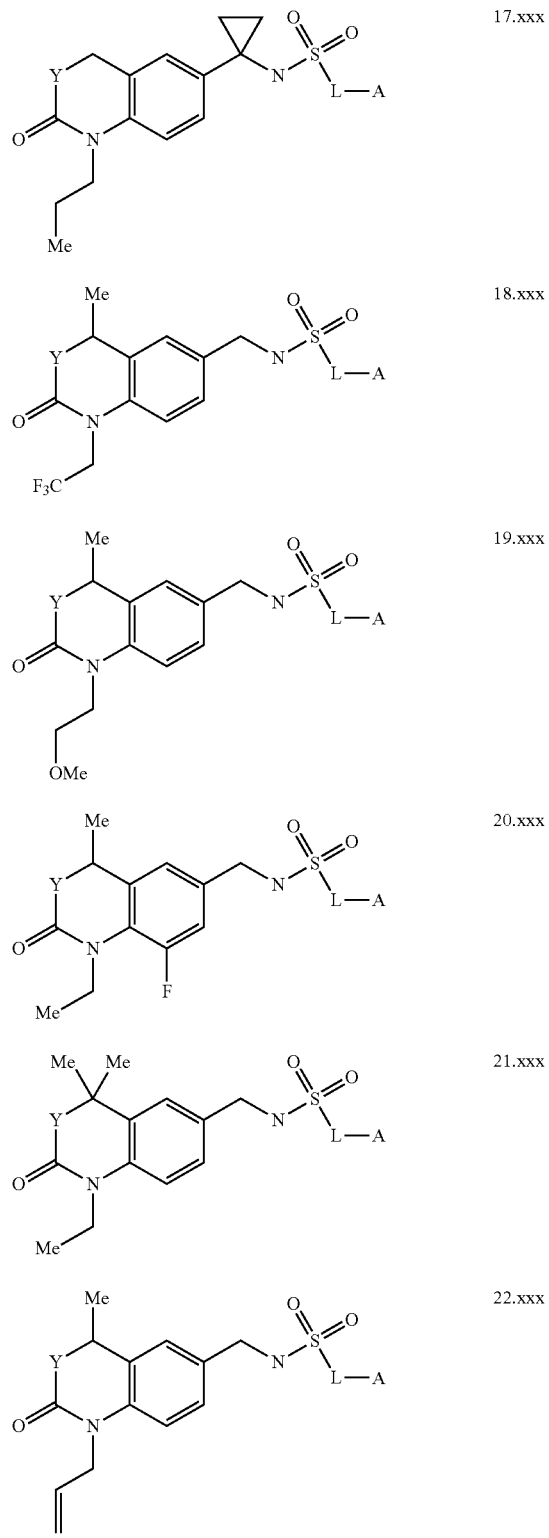

17.xxx 18.xxx 19.xxx 20.xxx 21.xxx 22.xxx

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

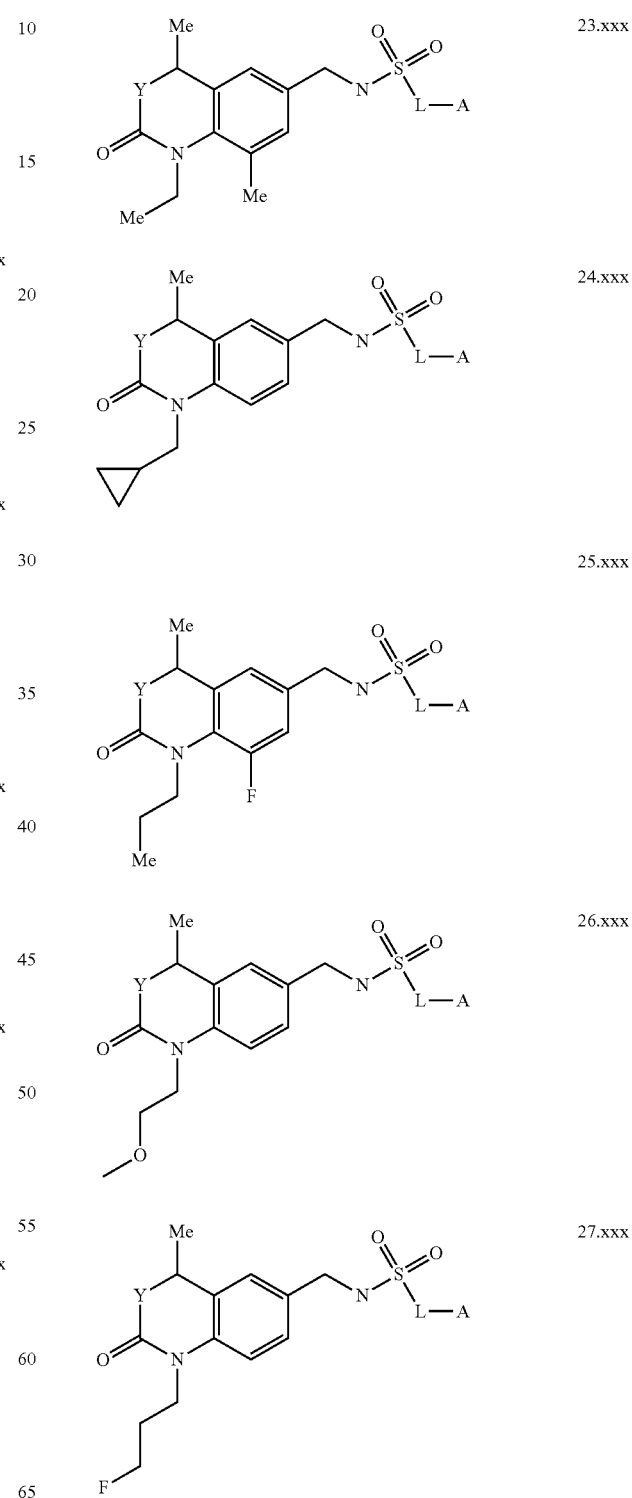

23.xxx 24.xxx 25.xxx 26.xxx 27.xxx

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

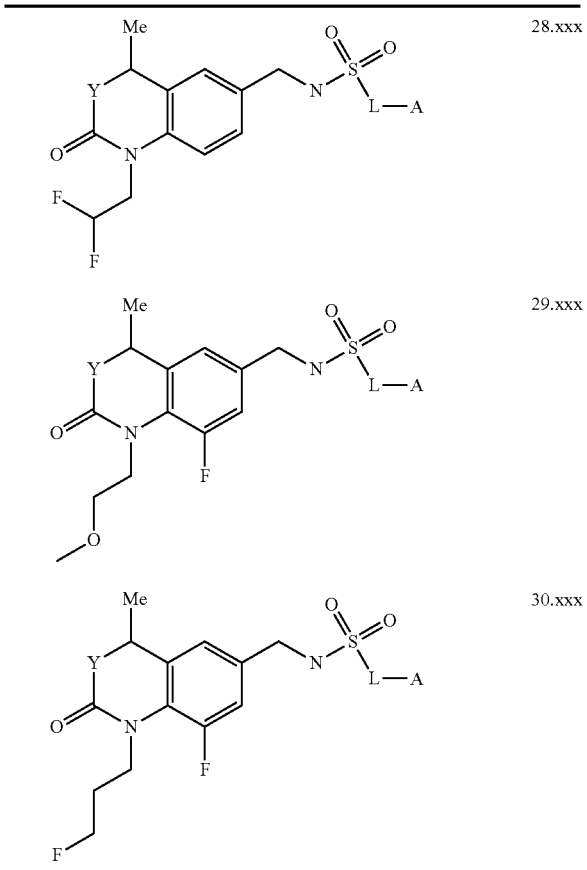

28.xxx 29.xxx 30.xxx

| Compound | L | A | Y |
|---|---|---|---|
| x.001 | bond | phenyl | O |
| x.002 | bond | 4-bromophenyl | O |
| x.003 | bond | 3-chlorophenyl | O |
| x.004 | bond | 4-chlorophenyl | O |
| x.005 | bond | 2,6-difluorophenyl | O |
| x.006 | bond | 2,4-difluorophenyl | O |
| x.007 | bond | 2-fluorophenyl | O |
| x.008 | bond | 3-fluorophenyl | O |
| x.009 | bond | 4-fluorophenyl | O |
| x.010 | bond | 4-methoxyphenyl | O |
| x.011 | bond | o-tolyl | O |
| x.012 | bond | p-tolyl | O |
| x.013 | bond | p-tolylmethyl | O |
| x.014 | bond | 2,4-dimethylphenyl | O |
| x.015 | bond | 4-(trifluoromethyl)phenyl | O |
| x.016 | bond | 4-isopropoxyphenyl | O |
| x.017 | bond | 2-bromophenyl | O |
| x.018 | bond | cyclopropyl | O |
| x.019 | bond | butyl | O |
| x.020 | bond | 4,4,4-trifluorobutyl | O |
| x.021 | —CH$_2$— | phenyl | O |
| x.022 | —CH$_2$— | 4-bromophenyl | O |
| x.023 | —CH$_2$— | 2-fluorophenyl | O |
| x.024 | —CH$_2$— | p-tolyl | O |
| x.025 | —CH$_2$— | 2,4-difluorophenyl | O |
| x.026 | —CH$_2$— | 2,6-difluorophenyl | O |
| x.027 | —CH$_2$— | 4-(cyclopropyl)phenyl | O |
| x.028 | —CH$_2$— | 4-nitrophenyl | O |
| x.029 | —CH$_2$— | 2,4-dichlorophenyl | O |
| x.030 | —CH$_2$— | 3-fluorophenyl | O |
| x.031 | —CH$_2$— | 4-chlorophenyl | O |
| x.032 | —CH$_2$— | 6-(trifluoromethyl)-3-pyridyl | O |
| x.033 | —CH$_2$— | 3-(trifluoromethyl)phenyl | O |
| x.034 | —CH$_2$— | —CH$_2$-methoxycarbonyl | O |
| x.035 | —CH$_2$—CH$_2$— | phenyl | O |
| x.036 | —CH=CH— | methyl | O |
| x.037 | bond | (5-methyl-2-thienyl) | O |
| x.038 | bond | propyl | O |
| x.039 | bond | (1-methylimidazol-4-yl) | O |
| x.040 | bond | (2,5-dichloro-3-thienyl) | O |
| x.041 | —CH$_2$—CH=CH— | methyl | O |
| x.042 | bond | 3,3,3-trifluoropropyl | O |
| x.043 | bond | 3-thienyl | O |
| x.044 | —CH=CH— | 3-chlorophenyl | O |
| x.045 | —CH=CH— | 3-bromophenyl | O |
| x.046 | —CH$_2$—CH=CH— | H | O |
| x.047 | bond | 2-thienyl | O |
| x.048 | bond | (5-chloro-2-thienyl) | O |
| x.049 | bond | 1-napthyl | O |
| x.050 | bond | 2-napthyl | O |
| x.051 | bond | 4-ethylphenyl | O |
| x.052 | bond | 4-propylphenyl | O |
| x.053 | bond | 4-cyclopropylphenyl | O |
| x.054 | bond | 2-fluoro-4-methylphenyl | O |
| x.055 | bond | phenyl | NH |
| x.056 | bond | 4-bromophenyl | NH |
| x.057 | bond | 3-chlorophenyl | NH |
| x.058 | bond | 4-chlorophenyl | NH |
| x.059 | bond | 2,6-difluorophenyl | NH |
| x.060 | bond | 2,4-difluorophenyl | NH |
| x.061 | bond | 2-fluorophenyl | NH |
| x.062 | bond | 3-fluorophenyl | NH |
| x.063 | bond | 4-fluorophenyl | NH |
| x.064 | bond | 4-methoxyphenyl | NH |
| x.066 | bond | o-tolyl | NH |
| x.067 | bond | p-tolyl | NH |
| x.068 | bond | p-tolylmethyl | NH |
| x.069 | bond | 2,4-dimethylphenyl | NH |
| x.070 | bond | 4-(trifluoromethyl)phenyl | NH |
| x.071 | bond | 4-isopropoxyphenyl | NH |
| x.072 | bond | 2-bromophenyl | NH |
| x.073 | bond | cyclopropyl | NH |
| x.074 | bond | butyl | NH |
| x.075 | bond | 4,4,4-trifluorobutyl | NH |
| x.076 | —CH$_2$— | phenyl | NH |
| x.077 | —CH$_2$— | 4-bromophenyl | NH |
| x.078 | —CH$_2$— | 2-fluorophenyl | NH |
| x.079 | —CH$_2$— | p-tolyl | NH |
| x.080 | —CH$_2$— | 2,4-difluorophenyl | NH |
| x.081 | —CH$_2$— | 2,6-difluorophenyl | NH |
| x.082 | —CH$_2$— | 4-(cyclopropyl)phenyl | NH |
| x.083 | —CH$_2$— | 4-nitrophenyl | NH |
| x.084 | —CH$_2$— | 2,4-dichlorophenyl | NH |
| x.085 | —CH$_2$— | 3-fluorophenyl | NH |
| x.086 | —CH$_2$— | 4-chlorophenyl | NH |
| x.087 | —CH$_2$— | 6-(trifluoromethyl)-3-pyridyl | NH |
| x.088 | —CH$_2$— | 3-(trifluoromethyl)phenyl | NH |
| x.089 | —CH$_2$— | —CH$_2$-methoxycarbonyl | NH |
| x.090 | —CH$_2$—CH$_2$— | phenyl | NH |
| x.091 | —CH=CH— | 3-bromophenyl | NH |
| x.092 | —CH$_2$—CH=CH— | H | NH |
| x.093 | bond | 2-thienyl | NH |
| x.094 | bond | (5-chloro-2-thienyl) | NH |
| x.095 | bond | 1-napthyl | NH |
| x.096 | bond | 2-napthyl | NH |
| x.097 | bond | 4-ethylphenyl | NH |
| x.098 | bond | 4-propylphenyl | NH |
| x.099 | bond | 4-cyclopropylphenyl | NH |
| x.100 | bond | 2-fluoro-4-methylphenyl | NH |

In one embodiment, the compounds of the present invention are applied in combination with an agriculturally acceptable adjuvant. In particular, there is provided a composition comprising a compound of the present invention and an agriculturally acceptable adjuvant. There may also be mentioned an agrochemical composition comprising a compound of the present invention.

The present invention provides a method of improving the tolerance of a plant to abiotic stress, wherein the method comprises applying to the plant, plant part, plant propagation material, or plant growing locus a compound, composition or mixture according to the present invention.

The present invention provides a method for regulating or improving the growth of a plant, wherein the method comprises applying to the plant, plant part, plant propagation material, or plant growing locus a compound, composition or mixture according to the present invention. In one embodiment, plant growth is regulated or improved when the plant is subject to abiotic stress conditions.

The present invention provides a method for enhancing the yield of a plant, wherein the method comprises applying to the plant, or plant growing locus a compound, composition or mixture according to the present invention.

The present invention also provides a method for inhibiting seed germination of a plant, comprising applying to the seed, or a locus containing seeds, a compound, composition or mixture according to the present invention.

The present invention also provides a method for safening a plant against phytotoxic effects of chemicals, comprising applying to the plant, plant part, plant propagation material, or plant growing locus a compound, composition or mixture according to the present invention.

Suitably the compound or composition is applied in an amount sufficient to elicit the desired response.

According to the present invention, "regulating or improving the growth of a crop" means an improvement in plant vigour, an improvement in plant quality, improved tolerance to stress factors, and/or improved input use efficiency.

An 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

An 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

An 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to biotic and/or abiotic stress factors, and in particular abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. In particular, the compounds or compositions of the present invention are useful to improve tolerance to drought stress.

An 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other effects of regulating or improving the growth of a crop include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compounds of the present invention can be used alone, but are generally formulated into compositions using formulation adjuvants, such as carriers, solvents and surface-active agents (SFAs). Thus, the present invention further provides a composition comprising a compound of the present invention and an agriculturally acceptable formulation adjuvant. There is also provided a composition consisting essentially of a compound of the present invention and an agriculturally acceptable formulation adjuvant. There is also provided a composition consisting of a compound of the present invention and an agriculturally acceptable formulation adjuvant.

The present invention further provides a crop yield enhancing composition comprising a compound of the present invention and an agriculturally acceptable formulation adjuvant. There is also provided a crop yield enhancing composition consisting essentially of a compound of the present invention and an agriculturally acceptable formulation adjuvant. There is also provided a crop yield enhancing composition consisting of a compound of the present invention and an agriculturally acceptable formulation adjuvant.

The present invention further provides a plant growth regulator composition comprising a compound of the present invention and an agriculturally acceptable formulation adjuvant. There is also provided a plant growth regulator composition consisting essentially of a compound of the present invention and an agriculturally acceptable formulation adjuvant. There is also provided a plant growth regulator composition consisting of a compound of the present invention and an agriculturally acceptable formulation adjuvant.

The present invention further provides a plant abiotic stress management composition comprising a compound of the present invention and an agriculturally acceptable formulation adjuvant. There is also provided a plant abiotic stress management composition consisting essentially of a compound of the present invention and an agriculturally acceptable formulation adjuvant. There is also provided a plant abiotic stress management composition consisting of a compound of the present invention and an agriculturally acceptable formulation adjuvant.

The present invention further provides a seed germination inhibitor composition comprising a compound of the present invention and an agriculturally acceptable formulation adjuvant. There is also provided a seed germination inhibitor composition consisting essentially of a compound of the present invention and an agriculturally acceptable formulation adjuvant. There is also provided a seed germination inhibitor composition consisting of a compound of the present invention and an agriculturally acceptable formulation adjuvant.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of the present invention and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultralow volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of the present invention.

Dustable powders (DP) may be prepared by mixing a compound of the present invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of the present invention with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the present invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the present invention and one or more powdered solid diluents or carriers, or from preformed blank granules by absorbing a compound of the present invention (or a solution thereof, in a suitable agent) in a porous granular material (such as pumice, attapulgite clays, fullers earth, kieselguhr, diatomaceous earths or ground corn cobs) or by adsorbing a compound of the present invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the present invention in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of the present invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the present invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the present invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the present invention. SCs may be prepared by ball or bead milling the solid compound of the present invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the present invention may be dry milled and added to water, containing agents hereinbefore described, to produce the desired end product.

Aerosol formulations comprise a compound of the present invention and a suitable propellant (for example n-butane). A compound of the present invention may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of the present invention and, optionally, a carrier or diluent therefor. The polymeric shell may be produced by either an interfacial polycondensation reaction or by a coacervation procedure.

The compositions may provide for controlled release of the compound of the present invention and they may be used for seed treatment. A compound of the present invention may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of the present invention. Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of the present invention). Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compound or composition of the present invention may be applied to a plant, part of the plant, plant organ, plant propagation material or a plant growing locus.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound or composition of the present invention may be applied pre-emergence or post-emergence. Suitably, where the composition is used to regulate the growth of crop plants or enhance the tolerance to abiotic stress, it may be applied post-emergence of the crop. Where the composition is used to inhibit or delay the germination of seeds, it may be applied pre-emergence.

The present invention envisages application of the compounds or compositions of the invention to plant propagation material prior to, during, or after planting, or any combination of these.

Although active ingredients can be applied to plant propagation material in any physiological state, a common approach is to use seeds in a sufficiently durable state to incur no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compounds of the present invention may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of the present invention according to the invention are generally applied at a rate of from 1 to 2000 g/ha, especially from 5 to 1000 g/ha. For seed treatment the rate of application is generally between 0.0005 and 150 g per 100 kg of seed.

The compounds and compositions of the present invention may be applied to dicotyledonous or monocotyledonous crops. Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®. Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compounds of the present invention may also be used to inhibit or delay the germination of seeds of non-crop plants, for example as part of an integrated weed control program. A delay in germination of weed seeds may provide a crop seedling with a stronger start by reducing competition with weeds. Alternatively compounds of the present invention may be used to delay the germination of seeds of crop plants, for example to increase the flexibility of timing of planting for the grower.

Normally, in the management of a crop a grower would use one or more other agronomic chemicals or biologicals in addition to the compound or composition of the present invention. There is also provided a mixture comprising a compound or composition of the present invention, and a further active ingredient.

Examples of agronomic chemicals or biologicals include pesticides, such as acaricides, bactericides, fungicides, herbicides, insecticides, nematicides, plant growth regulators, crop enhancing agents, safeners as well as plant nutrients and plant fertilizers. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops. The combination may also encompass specific plant traits incorporated into the plant using any means, for example conventional breeding or genetic modification.

The present invention also provides the use of a compound of formula (I), formula (II), formula (III), or formula (IV), or a composition comprising a compound according to formula (I), (II), (III), or (IV) and an agriculturally acceptable formulation adjuvant, for improving the tolerance of a plant to abiotic stress, regulating or improving the growth of a plant, inhibiting seed germination and/or safening a plant against phytotoxic effects of chemicals.

There is also provided the use of a compound, composition or mixture of the present invention, for improving the tolerance of a plant to abiotic stress, regulating or improving the growth of a plant, inhibiting seed germination and/or safening a plant against phytotoxic effects of chemicals.

The compounds of the invention may be made by the following methods.

PREPARATION EXAMPLES

Schemes 1-7 provide methods of preparing the compounds of formula (I), compounds of formula (II) and compounds of formula (III) of the present invention, wherein R4, R5 and R6 are H when present.

SCHEME 1:

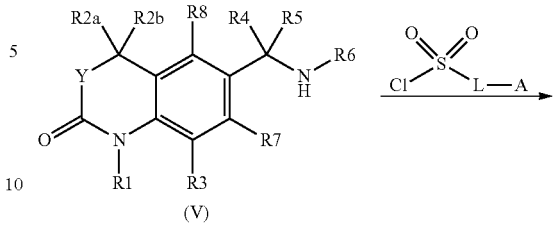

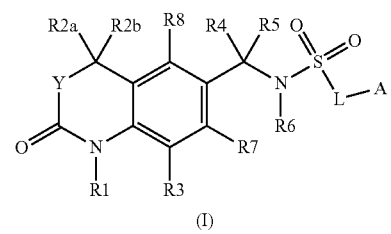

Compounds of formula (I) may be prepared from a compound of formula (V) by reaction with sulfonyl chloride of formula A-L-SO$_2$Cl. Such reactions are usually carried out in the presence of an organic base, such as N-ethyldiisopropylamine. For example, A-L-SO$_2$Cl can be benzenesulfonyl chloride, benzylsulfonyl chloride or butylsulfonyl chloride. Compounds of formula A-L-SO$_2$Cl are commercially available or can be made by methods known to a person skilled in the art.

SCHEME 2:

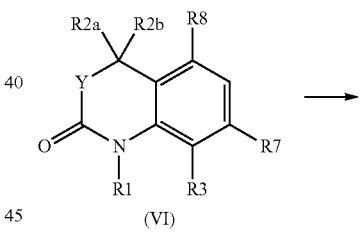

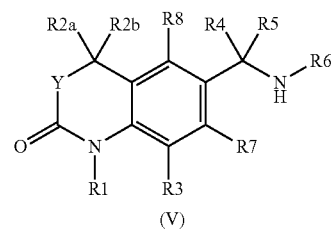

Compounds of formula (V), wherein R4, R5 and R6 are H, may be prepared from a compound of formula (VI) by reaction with 2-chloro-N-(hydroxymethyl)acetamide in a solvent such as acetic acid, and optionally in the presence of stronger acid such as sulfuric acid, followed by hydrolysis of the resulting 2-chloroacetamide with an acid such as HCl in an alcoholic solvent. Compound (V) can be obtained as its hydrochloride salt or a free amine after neutralization with a base.

SCHEME 3:

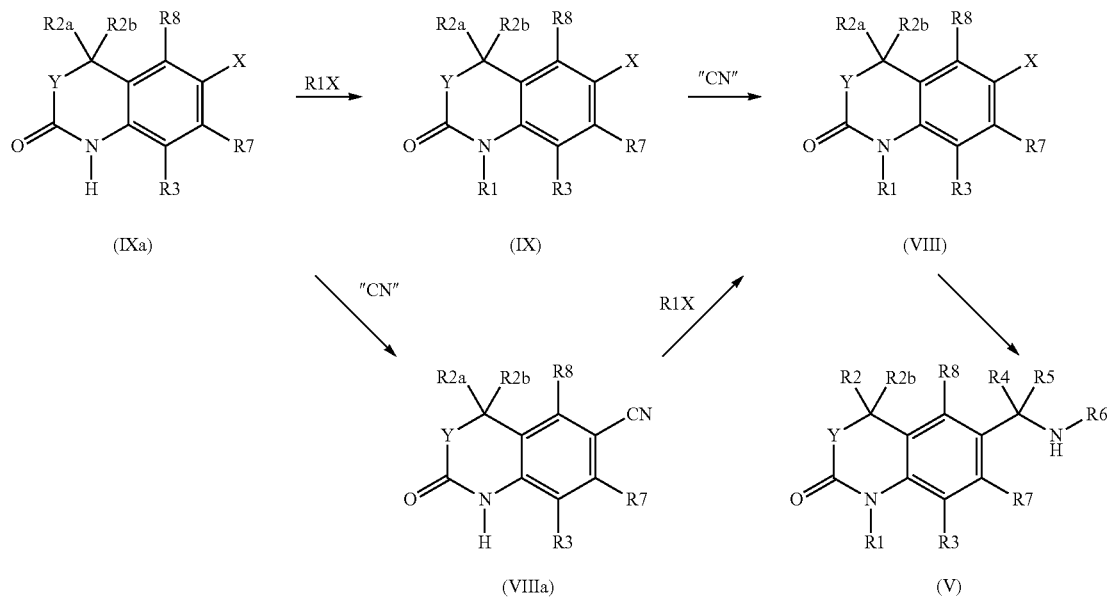

Compounds of formula (V), wherein R4, R5 and R6 are H, may be prepared from a compound of formula (VIII) by reduction of the cyano moiety under hydrogen atmosphere in the presence of a catalyst such as palladium on charcoal, or by reducing agent such as sodium borohydride in the presence of a catalyst such as nickel chloride or cobalt chloride for example.

The compound of formula (VIII) may be obtained from a compound of formula (IX) wherein X is a leaving group such as Cl or Br, I or OTf by a coupling reaction with a cyanide salt such as CuCN, NaCN, $K_3[Fe(CN)_6]$, optionally in the presence of a catalyst such as palladium (0) or copper, optionally with an additional ligand as described in the literature (see Zanon et al, *J. Am. Chem Soc.* 2003, 125, 2890-2891; Buchwald, S & all, *Angew. Chem. Int. Ed.* 2013, 52: 10035-10039).

The compound of formula (IX) may be obtained from a compound of formula (IXa) by reaction with an alkylating agent of formula R1-X, wherein X is a leaving group such as halogen, mesylate, triflate or tosylate. For example, R1-X can be propyl iodide, ethyl iodide, allyl bromide, or methyl iodide. Such reactions are usually carried out in the presence of a base, and optionally in the presence of a nucleophilic catalyst.

Alternatively, compound of formula (VIII) may be obtained from a compound of formula (VIIIa) by reaction with an alkylating agent of formula R1-X, wherein X is a leaving group such as halogen, mesylate, triflate or tosylate. For example, R1-X can be propyl iodide, ethyl iodide, allyl bromide, or methyl iodide. Such reactions are usually carried out in the presence of a base, and optionally in the presence of a nucleophilic catalyst.

Compound of formula (VIIIa) may be prepared from compound (IXa) wherein X is a leaving group such as Cl or Br, I or OTf by a coupling reaction with a cyanide salt as described for compound (VIIIa).

SCHEME 4:

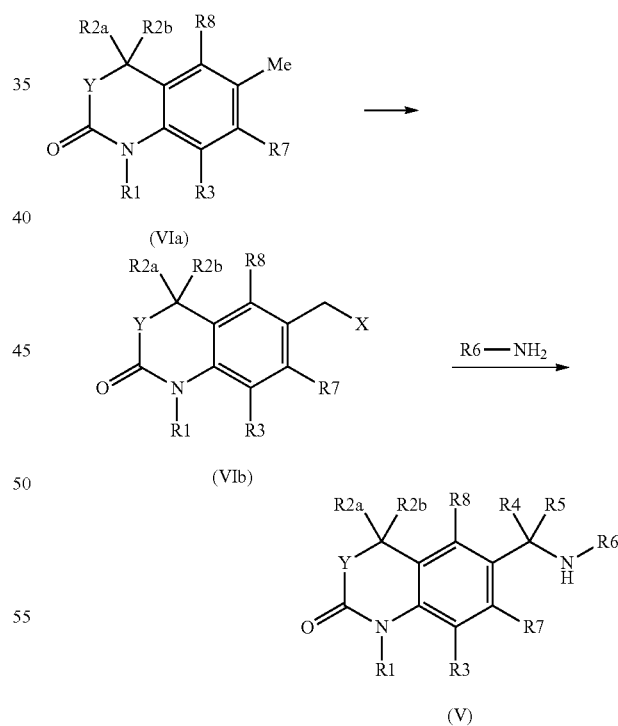

Compounds of formula (V), wherein R4 and R5 are H, may be prepared from a compound of formula (VIb) wherein X is a leaving group such as halogen, by reaction with an amine of formula R6-NH$_2$ or its hydrochloride salt of formula R6-NH$_3$Cl, optionally in the presence of a base such as triethyl amine or diisopropylamine. For example, R6NH$_2$ can be ammonia, methyl amine or ethyl amine.

The compound of formula (VIb) may be obtained from a compound of formula (VIa) wherein X is a leaving group such as Cl or Br, by radical reaction with N-bromosuccinimide or N-chlorosuccinimide in the presence of an initiator such as AIBN or dibenzoyl peroxide.

SCHEME 5:

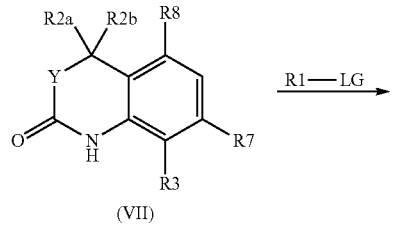

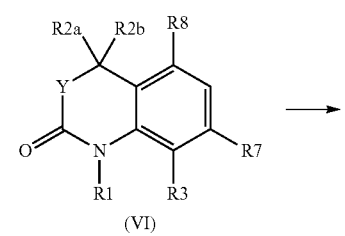

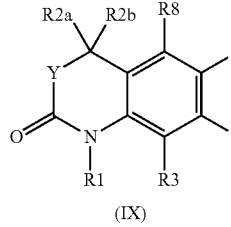

Compounds of formula (VII) are commercially available or can be made by methods known to a person skilled in the art. Compounds of formula (VI) may be prepared from a compound of formula (VII) by reaction with an alkylating agent of formula R1-LG, wherein LG is a leaving group such as halogen, mesylate, triflate or tosylate. For example, R1-LG can be propyl iodide, ethyl iodide, allyl bromide or methyl iodide. Such reactions are usually carried out in the presence of a base, and optionally in the presence of a nucleophilic catalyst. Compound of formula (IX), wherein X is a halogen such as Cl, Br or I can be obtained from a compound of formula (VI) by reaction with the corresponding N—X succinimide as for example N-bromosuccinimide when X is Br.

SCHEME 6:

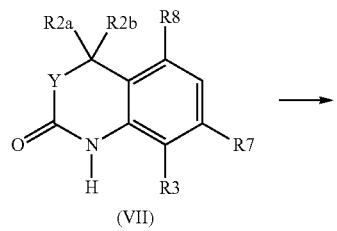

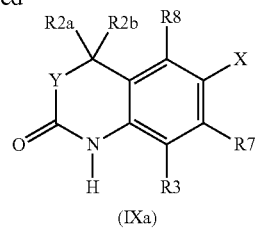

Compound of formula (IXa), wherein X is a halogen such as Cl, Br or I can be obtained from a compound of formula (VII) by reaction with the corresponding N—X succinimide as for example N-bromosuccinimide when X is Br.

SCHEME 7:

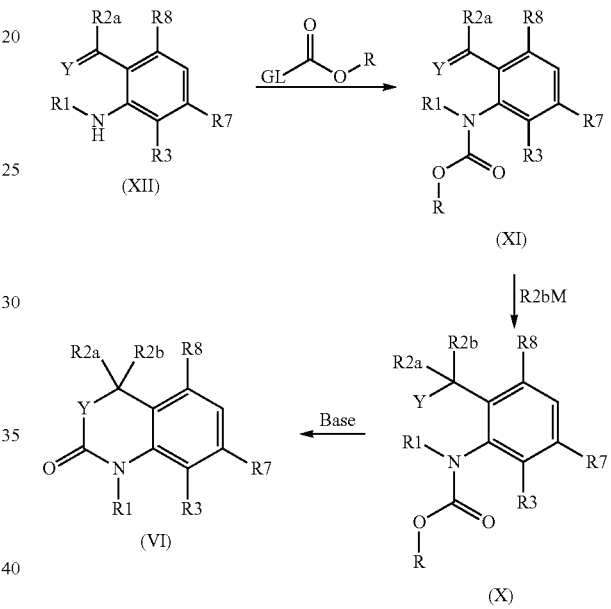

Compounds of formula (VI) can be made from compound of formula (X) by reaction with a base such as a carbonate or sodium hydride. Compounds of formula (X), wherein R2b is H and R is a C1-C6 alkyl group can be made from a compound of formula (XI) by reaction of a metal hydride of formula R2b H such as sodium borohydride. Compounds of (XI) wherein R is a C1-C6 alkyl group can be made from a compound of formula (XII) by reaction with a carbonate of formula CO(OR)$_2$ or a alkylchloroformate of formula CO(OR)Cl in the presence of an organic base such as pyridine or triethylamine. Compounds of formula (XII) are commercially available or can be made by methods known to a person skilled in the art.

Example P1: Preparation of N-[(2-oxo-1-propyl-4H-3,1-benzoxazin-6-yl)methyl]benzenesulfonamide (Compound 3.001)

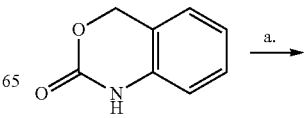

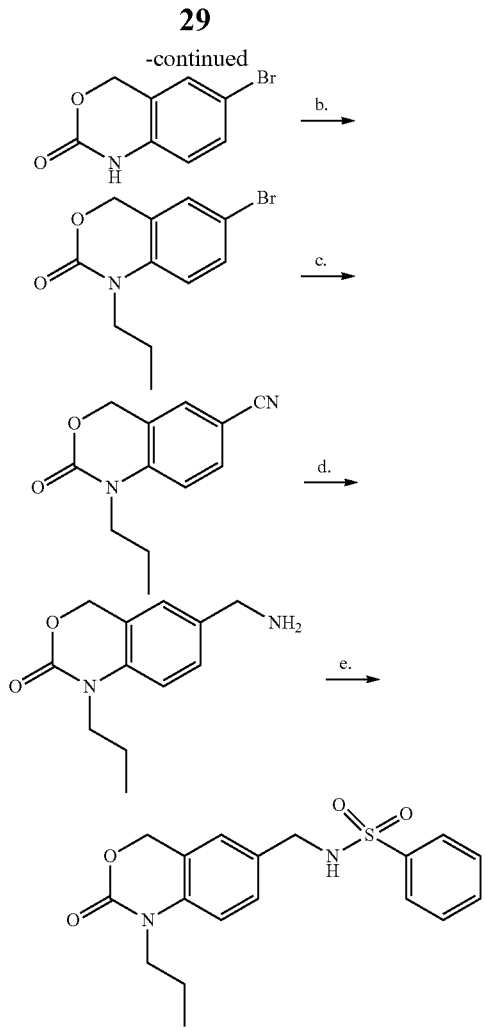

a. 6-bromo-4H-3,1-benzoxazin-2-one 1,4-Dihydro-3,1-benzoxazin-2-one (1.00 g, 6.70 mmol) (prepared as in Synlett, 1999, (2), 207-209) was dissolved in dimethylformamide (13 mL) and cooled to 0° C. N-Bromosuccinimide (1.33 g, 7.38 mmol) was added in portions at 0° C. The reaction mixture was stirred at 40° C. for 3 h. The reaction mixture was poured on water and the white solid was filtered, washed with water and dried to give 6-bromo-4H-3,1-benzoxazin-2-one as a white powder (1.44 g, 94%). $^1$H NMR (chloroform-d3) δ: 8.55-8.85 (s, 1H), 7.39 (dd, 1H), 7.27 (d, 1H), 6.85 (, 1H), 5.30 (s, 2H).

b. 6-bromo-1-propyl-4H-3,1-benzoxazin-2-one

6-Bromo-4H-3,1-benzoxazin-2-one (500 mg, 2.19 mmol) was dissolved in dimethylformamide (11 mL) and potassium carbonate (0.459 g, 3.289 mmol) was added followed by 1-bromopropane (0.400 mL, 4.38 mmol) dropwise. The reaction mixture was heated to 60° C. and stirred for 4 hours. The reaction mixture was poured into ice/water and extracted with ethyl acetate (2×20 mL). The combined organic layers were washed with brine (3×20 mL), dried over Na$_2$SO$_4$ and concentrated. The crude oil was purified by flash chromatography to give 6-bromo-1-propyl-4H-3,1-benzoxazin-2-one as a colourless solid (390 mg, 66%). $^1$H NMR (chloroform-d3) Shift: 7.45 (d, 1H), 7.27 (s, 1H), 6.82 (d, 1H), 5.15 (s, 2H), 3.80-3.88 (m, 2H), 1.69-1.84 (m, 2H), 1.00 (t, 3H).

c. 2-oxo-1-propyl-4H-3,1-benzoxazine-6-carbonitrile

6-Bromo-1-propyl-4H-3,1-benzoxazin-2-one (0.175 g, 0.647 mmol) was dissolved in 1,4-dioxane (1.6 mL) and water (1.6 mL). Potassium acetate (9.6 mg, 0.097 mmol) and potassium hexacyanoferrate(II) trihydrate (0.119 g, 0.323 mmol) were added and the solution was purged with argon. tBuBrettphos Pd G3 (Sigma-Aldrich, 29 mg, 0.0324 mmol) and tBuBrettphos (15 mg, 0.032 mmol) were added under argon. The reaction mixture was heated to reflux and stirred for 1 h. The reaction mixture was cooled to room temperature and brine was added. It was extracted 3 times with ethyl acetate, the organic layers were combined, dried over Na$_2$SO$_4$ and the solvent was evaporated. The crude compound was purified by flash chromatography to give 2-oxo-1-propyl-4H-3,1-benzoxazine-6-carbonitrile as a pale yellow solid (62 mg, 44%). $^1$H NMR (chloroform-d3) Shift: 7.61-7.69 (d, 1H), 7.43 (s, 1H), 7.02 (d, 1H), 5.22 (s, 2H), 5.11-5.19 (m, 1H), 3.81-3.94 (m, 2H), 1.71-1.87 (m, 2H), 1.02 (t, 3H).

d. 6-(aminomethyl)-1-propyl-4H-3,1-benzoxazin-2-one hydrochloride

2-Oxo-1-propyl-4H-3,1-benzoxazine-6-carbonitrile (0.078 g, 0.360 mmol) was dissolved in a mixture of ethanol (3.6 mL) and ethyl acetate (3.6 mL) and was purged with argon. Hydrochloric acid (32 mass % in H$_2$O, 0.265 mL, 2.70 mmol) was added followed by Pd/C 10% (0.008 g, 0.007 mmol). The reaction mixture was placed under an atmosphere of hydrogen (balloon) and was stirred for 12 h. The atmosphere was changed to argon and more Pd/C (30 mg) was added. The atmosphere was changed again to hydrogen (balloon, 1 atm.) and the reaction mixture was stirred for 4 h. The reaction mixture was purged with argon and was filtered over Celite®. Solvents were evaporated and tert-butyl methyl ether was added. The white solid was filtered to give 6-(aminomethyl)-1-propyl-4H-3,1-benzoxazin-2-one hydrochloride (0.092 g, 99%) as a pale yellow solid. $^1$H NMR (methanol-d4) δ: 7.47 (br d, 1H), 7.32 (s, 1H), 7.18 (br d, 1H), 5.25 (s, 2H), 4.10 (s, 2H), 3.88 (br m, 2H), 1.63-1.80 (m, 2H), 0.98 (t, 3H).

e. N-[(2-oxo-1-propyl-4H-3,1-benzoxazin-6-yl)methyl]benzenesulfonamide (Compound 3.001)

6-(aminomethyl)-1-propyl-4H-3,1-benzoxazin-2-one hydrochloride (0.086 g, 0.335 mmol) was suspended in ethyl acetate (3 mL) and diisopropylethyl amine (0.143 mL, 0.837 mmol) was added, followed by benzenesulfonyl chloride (0.067 g, 0.368 mmol). The reaction mixture was stirred at room temperature for 90 min. Water and brine were added and the aqueous layer was extracted with ethyl acetate. The organic layers were combined, dried over Na$_2$SO$_4$ and the solvent was evaporated to give the crude compound, which was purified on silica gel to give N-[(2-oxo-1-propyl-4H-3, 1-benzoxazin-6-yl)methyl]benzenesulfonamide as a colorless solid (0.052 g, 43%). $^1$H NMR (chloroform-d3) δ: 7.87 (d, 2H), 7.44-7.66 (m, 3H), 7.09-7.25 (d, 1H), 6.97 (s, 1H), 6.84 (d, 1H), 5.09 (s, 2H), 4.77 (br m, 1H), 4.13 (d, 2H), 3.74-3.89 (m, 2H), 1.72 (sxm, 2H), 0.99 (t, 3H). LC-MS: RT 0.89, ES+ (392, M−H+).

Example P2: Preparation of N-[(8-fluoro-4-methyl-2-oxo-1-propyl-4H-3,1-benzoxazin-6-yl)methyl]benzenesulfonamide (Compound 25.001)

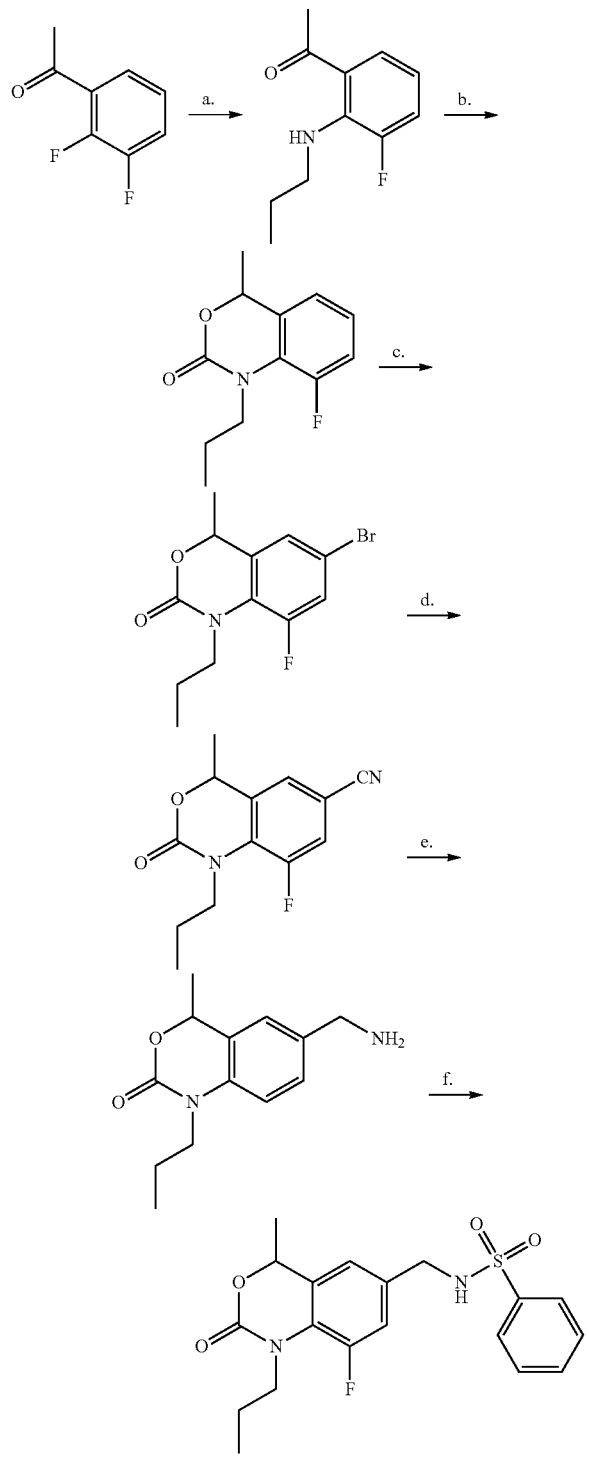

Step a: 1-[3-fluoro-2-(propylamino)phenyl]ethanone

A solution of 1-(2,3-difluorophenyl)ethanone (7.81 g, 50 mmol), $K_2CO_3$ (10.4 g, 75 mmol) and propylamine (12.3 mL. 150 mmol) in DMF (55 mL) was heated at 50° C. for 42 h. The reaction mixture was then poured into ice water and extracted 3 times with a 1/1 mixture of ethyl acetate and cyclohexane. The combined organic layer was washed with brine and concentrated under vacuo to give 1-[3-fluoro-2-(propylamino)phenyl]ethanone (9.38 g, 96%) as a pale green oil.

LCMS: 1.09 min; ES+ 196 (M+H+); 1H NMR (400 MHz, CHLOROFORM-d) 8.78 (s, 1H), 7.52 (d, 1H), 7.08 (dd, 1H), 6.51 (m, 1H), 3.42 (m, 2H), 2.52 (s, 3H), 1.61 (m, 2H), 0.94 (t, 3H).

Step b: 8-fluoro-4-methyl-1-propyl-4H-3,1-benzoxazin-2-one

To a solution of 1-[3-fluoro-2-(propylamino)phenyl]ethanone (9.35 g, 47 mmol) in dioxane (95 mL) was added $K_2CO_3$ (7.74 g, 57.5 mmol) and ethyl chloroformate (5.67 mL, 57.5 mmol). The suspension was stirred at 85° C. for 5 h, cooled down to room temperature and filtered. The solvent was evaporated and the crude oil was purified by flash chromatography to give ethyl N-(2-acetyl-6-fluoro-phenyl)-N-propyl-carbamate (11.3 g, 88%) as an oil.

To a solution of ethyl N-(2-acetyl-6-fluoro-phenyl)-N-propyl-carbamate (4.01 g, 15.0 mmol) in methanol (38 mL) was added portionwise sodium borohydride (567 mg, 15.0 mmol) at 0° C. The solution was stirred for 30 min and then quenched with a saturated solution of $NH_4Cl$. The solution was extracted two times with ethyl acetate and the organic layers were washed with water, brine, dried over $Na_2SO_4$, filtered and evaporated to give ethyl N-[2-fluoro-6-(1-hydroxyethyl)phenyl]-N-propyl-carbamate (4.06 g, quant) as an oil which was used directly in the next step.

To a solution of ethyl N-[2-fluoro-6-(1-hydroxyethyl)phenyl]-N-propyl-carbamate (4.04 g, 15.0 mmol) in THF (75 mL) under Ar cooled at −20° C. was added NaH (55% in mineral oil, 654 mg, 15.0 mmol) and the solution was stirred for 15 min at 0° C. The reaction mixture was then quenched with iPrOH (1 mL) followed by a saturated solution of $NH_4Cl$. The solution was extracted two times with ethyl acetate and the organic layers were washed with water, brine, dried over $Na_2SO_4$, filtered and evaporated. The crude compound was crystallized from pentane to give 8-fluoro-4-methyl-1-propyl-4H-3,1-benzoxazin-2-one (2.57 g, 77%).

LCMS: 0.96 min; ES+ 224 (M+H+); 1H NMR (400 MHz, CHLOROFORM-d) 7.10-7.15 (m, 2H), 6.91 (m, 1H), 5.25 (q, 1H), 3.98 (m, 2H), 1.75 (m, 2H), 1.66 (d, 3H), 0.94 (t, 3H).

Step c: 6-Bromo-8-fluoro-4-methyl-1-propyl-4H-3,1-benzoxazin-2-one

To a solution of 8-fluoro-4-methyl-1-propyl-4H-3,1-benzoxazin-2-one (1.10 g, 4.93 mmol) in trifluoroacetic acid (11 mL) was added at room temperature N-bromosuccinimide (1.33 g. 7.39 mmol) and the reaction mixture was heated to 60° C. for 16 h. The reaction mixture was then cooled down to room temperature and poured into a cold aqueous solution of NaOH (2 M) and sodium thiosulfate was added. The solution was extracted two times with ethyl acetate and the organic layers were washed with water, brine, dried over $Na_2SO_4$, filtered and evaporated. The crude compound was crystallized from dichloromethane and petrolether to give 6-bromo-8-fluoro-4-methyl-1-propyl-4H-3,1-benzoxazin-2-one (780 mg, 52%).

LCMS: 1.08 min; ES+ 302/304 (M+H+); 1H NMR (400 MHz, CHLOROFORM-d) 7.22 (s, 1H), 7.07 (s, 1H), 5.21 (q, 1H), 3.96 (m, 2H), 1.71 (m, 2H), 1.65 (d, 3H), 0.93 (t, 3H).

Step d: 8-fluoro-4-methyl-2-oxo-1-propyl-4H-3,1-benzoxazine-6-carbonitrile 6-bromo-8-fluoro-4-methyl-1-propyl-4H-3,1-benzoxazin-2-one (0.400 g, 1.32 mmol) was dissolved in 1,4-dioxane (3.3 mL) and water (3.3 mL). Potassium acetate (19.7 mg, 0.199 mmol) and potassium hexacyanoferrate(II) trihydrate (0.244 g, 0.323 mmol) were added and the solution was purged with argon. tBuBrettphos Pd G3 (Sigma-Aldrich, 59 mg, 0.066 mmol) and tBuBrettphos (32 mg, 0.066 mmol) were added under argon. The reaction mixture was heated to reflux and stirred for 2 h. The reaction mixture was cooled to room temperature and brine was added. It was extracted 3 times with ethyl acetate, the organic layers were combined, dried over $Na_2SO_4$ and the solvent was evaporated. The crude compound was purified by flash chromatography to give 8-fluoro-4-methyl-2-oxo-1-propyl-4H-3,1-benzoxazine-6-carbonitrile as a pale yellow solid (355 mg, quant).

LCMS: 0.93 min; ES+ 259 (M+H+); 1H NMR (400 MHz, CHLOROFORM-d) δ=7.42 (d, 1H), 7.24 (s, 1H), 5.28 (q, 1H), 4.08-3.92 (m, 2H), 1.82-1.65 (m, 2H), 1.71 (d, 3H), 0.97 (t, 3H).

Step e: 6-(aminomethyl)-8-fluoro-4-methyl-1-propyl-4H-3,1-benzoxazin-2-one

8-Fluoro-4-methyl-2-oxo-1-propyl-4H-3,1-benzoxazine-6-carbonitrile (0.328 g, 1.32 mmol) was dissolved in a mixture of ethanol (7 mL) and ethyl acetate (7 mL) and was purged with argon. Hydrochloric acid (32 mass % in $H_2O$, 0.303 mL, 9.90 mmol) was added followed by Pd/C 10% (0.033 g, 0.031 mmol). The reaction mixture was placed under an atmosphere of hydrogen (balloon) and was stirred for 12 h. The atmosphere was changed to argon and more Pd/C (30 mg) was added. The atmosphere was changed again to hydrogen (balloon, 1 atm.) and the reaction mixture was stirred for 4 h. The reaction mixture was purged with argon and was filtered over Celite®. Sovents were evaporated and tert-butyl methyl ether was added. The white solid was filtered to give 6-(aminomethyl)-8-fluoro-4-methyl-1-propyl-4H-3,1-benzoxazin-2-one (0.320 g, 82%) as a pale yellow solid. 1H NMR (400 MHz, METHANOL-d4) δ ppm 0.97 (t, 3H), 1.70 (d, 3H), 1.76 (m, 2H), 3.95 (t, 2H), 4.15 (s, 2H), 5.44 (q, 1H), 7.21 (d, 1H), 7.36 (dd, 1H).

Step f: N-[(8-fluoro-4-methyl-2-oxo-1-propyl-4H-3,1-benzoxazin-6-yl)methyl]benzenesulfonamide (Compound 25.001)

6-(Aminomethyl)-8-fluoro-4-methyl-1-propyl-4H-3,1-benzoxazin-2-one (0.130 g, 0.450 mmol) was suspended in ethyl acetate (4 mL) and diisopropylethyl amine (0.193 mL, 1.13 mmol) was added, followed by benzenesulfonyl chloride (0.103 g, 0.585 mmol). The reaction mixture was stirred at room temperature for 90 min. Water and brine were added and the aqueous layer was extracted with ethyl acetate. The organic layers were combined, dried over $Na_2SO_4$ and the solvent was evaporated to give the crude compound, which was purified on silica gel to give N-[(8-fluoro-4-methyl-2-oxo-1-propyl-4H-3,1-benzoxazin-6-yl)methyl]benzenesulfonamide as a colorless solid (0.160 mg, 90%). 0.92 (t, 3H), 1.60 (d, 3H), 1.62-1.78 (m, 2H), 3.88-4.00 (m, 2H), 4.09-4.15 (m, 2H), 4.91 (br t, 1H), 5.17 (q, 1H), 6.77 (s, 1H), 6.93 (dd, 1H), 7.50-7.55 (m, 2H), 7.57-7.63 (m, 1H), 7.83-7.89 (m, 2H).

Example P3: Preparation of 5-chloro-N-[[1-(2-methoxyethyl)-4-methyl-2-oxo-4H-3,1-benzoxazin-6-yl]methyl]thiophene-2-sulfonamide (Compound 26.048)

Step a: ethyl N-(2-acetylphenyl)carbamate

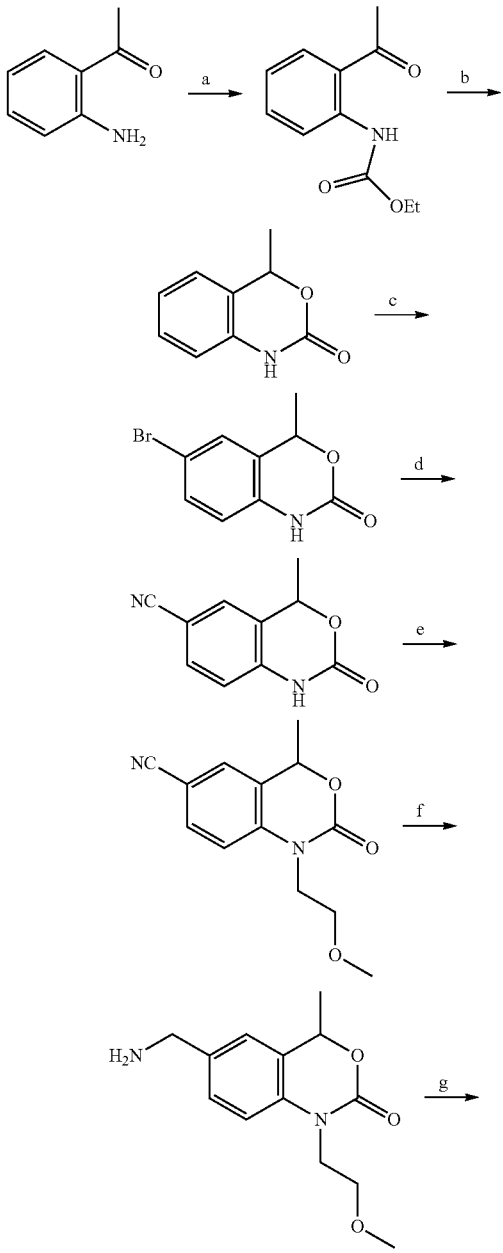

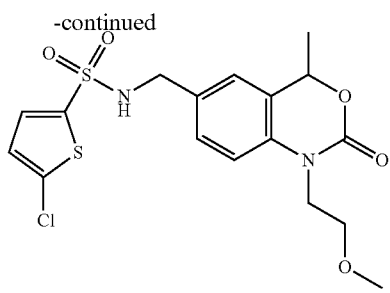

2-Acetylaniline (10.0 g, 72.5 mmol) was dissolved in ethyl acetate (72 mL) and cooled to 0° C. Ethyl chloroformate (7.86 mL, 79.8 mmol) was added followed by pyridine dropwise (6.22 mL, 76.1 mmol). Water was added and the reaction was extracted with ethyl acetate. The organic layers were washed with 1N HCl, dried and concentrated to give ethyl N-(2-acetylphenyl)carbamate (15.0 g, quant.) as an orange solid.

LCMS: 0.97 min; ES+ 208 (M+H+); $^1$H NMR (CHLOROFORM-d, 400 MHz): δ (ppm) 11.15 (br s, 1H), 8.49 (d, 1H), 7.88 (d, 1H), 7.55 (t, 1H), 7.06 (t, 1H), 4.23 (q, 2H), 2.66 (s, 3H), 1.33 (t, 3H).

Step b: 4-methyl-1,4-dihydro-3,1-benzoxazin-2-one

Ethyl N-(2-acetylphenyl)carbamate (1.00 g, 4.83 mmol) was solved in THF (25 mL) and added sodium borohydride (0.369 g, 9.65 mmol). The reaction mixture was stirred for 5 h at room temperature. The reaction mixture was quenched with water (10 mL) and then 10 mL of HCl (1 M) were added very slowly. The reaction mixture was then extracted with ethyl acetate (3×25 mL) and washed with brine, dried and concentrated to give a crude oil of ethyl N-[2-(1-hydroxyethyl)phenyl]carbamate and 4-methyl-1,4-dihydro-3,1-benzoxazin-2-one. The crude mixture was taken up in acetonitrile (20 mL) and potassium carbonate (0.667 g, 4.83 mmol) was added. The suspension was heated to reflux for 5 h, cooled down to room temperature, filtered and concentrated. The crude solid was purified by flash chromatography to give 4-methyl-1,4-dihydro-3,1-benzoxazin-2-one (0.727 g, 92%) as a white solid.

LCMS: 0.64 min; ES+ 164 (M+H+); $^1$H NMR (CHLOROFORM-d, 400 MHz): δ (ppm) 8.79 (br s, 1H), 7.44 (t, 1H), 7.19-7.31 (m, 2H), 7.09 (d, 1H), 5.65-5.76 (q, 1H), 1.90 (d, 3H).

Step c: 6-bromo-4-methyl-1,4-dihydro-3,1-benzoxazin-2-one 4-methyl-1,4-dihydro-3,1-benzoxazin-2-one (13.7 g, 84.0 mmol) was dissolved in dimethylformamide (340 mL) and cooled to 0° C. N-Bromosuccinimide (19.6 g, 109 mmol) was added in portions at 0° C. Reaction was warmed up to room temperature and stirred for 15 h. The reaction mixture was poured on water/ice and a suspension was formed. It was filtered and washed with water, and dried to give the crude 6-bromo-4-methyl-1,4-dihydro-3,1-benzoxazin-2-one (18.7 g, 92%) as a beige powder.

LCMS: 0.79 min; ES+ 243/245 (M+H+); 1H NMR (400 MHz, CHLOROFORM-d) d ppm 1.68—(d, 3H), 5.45 (q, 1H), 6.72 (d, 1H), 7.22 (s, 1H), 7.35 (d, 1H), 8.52 (brs, 1H).

Step d: 4-methyl-2-oxo-1,4-dihydro-3,1-benzoxazine-6-carbonitrile

6-Bromo-4-methyl-1,4-dihydro-3,1-benzoxazin-2-one (3.33 g, 13.8 mmol), potassium acetate (0.205 g, 2.06 mmol) and potassium hexacyanoferrate(II) trihydrate (2.53 g, 6.88 mmol) were suspended in dioxane (34 mL) and water (34 mL) and degassed with argon. tBuBrettphos Pd G3 (0.245 g, 0.275 mmol) and tBuBrettphos (0.133 g, 0.275 mmol) were added and the reaction mixture was heated to 110° C. for 2 h. tBuBrettphos Pd G3 (0.245 g, 0.275 mmol) and tBuBrettphos (0.133 g, 0.275 mmol) were added to the reaction mixture which was stirred for a further 1 h. It was cooled to room temperature, brine was added and it was extracted 3 times with ethyl acetate. The combined organic layers were combined, dried over Na$_2$SO$_4$ and the solvent was evaporated to give the crude which was crystallised from tert butyl methyl ether to give 4-methyl-2-oxo-1,4-dihydro-3,1-benzoxazine-6-carbonitrile (1.92 g, 74%) as a beige solid.

LCMS: 0.60 min; ES+ 189 (M+H+); $^1$H NMR (400 MHz, DMSO-d) d ppm 1.56 (d, 3H), 5.56 (q, 1H), 7.00 (d, 1H), 7.72 (m, 2H), 10.62 (brs, 1H).

Step e: 1-(2-methoxyethyl)-4-methyl-2-oxo-4H-3,1-benzoxazine-6-carbonitrile 6-cyano-4-methyl-1,4-dihydro-3,1-benzoxazin-2-one (600 mg, 3.18 mmol) was dissolved in dimethylformamide (13 mL) and potassium carbonate (1.11 g, 7.97 mmol) was added. 1-bromo-2-methoxy-ethane (0.473 mL, 4.78 mmol) was added dropwise and the reaction mixture was heated to 50° C. and stirred for 2 h. 1-Bromo-2-methoxy-ethane (0.473 mL) were added and it was stirred for another 1 h. Water and ethyl acetate were added and it was extracted with ethyl acetate. The organic layers were combined, washed twice with a 5% LiCl-solution and once with brine, dried over Na$_2$SO$_4$ and the solvent was evaporated to give the crude (1.29 g) as a yellow oily solid which was purified by flash chromatography to give 6-cyano-1-(2-methoxyethyl)-4-methyl-4H-3,1-benzoxazin-2-one (0.713 g, 90%) as an oil.

$^1$H NMR (400 MHz, CHLOROFORM-d) d ppm 1.68 (d, 3H), 3.32 (s, 3H), 3.68 (dd, 2H), 4.05 (m, 2H), 5.38 (q, 1H), 7.29 (d, 1H), 7.40 (s, 1H), 7.63 (d, 1H).

Step f: 6-(aminomethyl)-1-(2-methoxyethyl)-4-methyl-4H-3,1-benzoxazin-2-one

To a solution of 1-(2-methoxyethyl)-4-methyl-2-oxo-4H-3,1-benzoxazine-6-carbonitrile (500 mg, 2.030 mmol) in methanol (20 mL) was added Nickel(II) chloride hexahydrate (96 mg, 0.406 mmol). Then the reaction mixture was cooled to 0° C. and sodium borohydride (313 mg, 8.12 mmol) was added portionwise. The reaction mixture was stirred for 2 h at room temperature. The reaction mixture was filtered over Celite® and the filter cake was washed with methanol. The solvent was removed and the residue was partitioned between 1N HCl and ethyl acetate. The aqueous layer was then neutralized with NaOH (2M) and extracted with ethyl acetate. The organic layer was dried over Na$_2$SO$_4$ and concentrated to give 6-(aminomethyl)-1-(2-methoxyethyl)-4-methyl-4H-3,1-benzoxazin-2-one (356 mg, 70%). LCMS: 0.24 min; ES+ 250 (M-NH2).

Step g: 5-chloro-N-[[1-(2-methoxyethyl)-4-methyl-2-oxo-4H-3,1-benzoxazin-6-yl]methyl]thiophene-2-sulfonamide (Compound 26.048)

To a solution of 6-(aminomethyl)-1-(2-methoxyethyl)-4-methyl-4H-3,1-benzoxazin-2-one (119 mg, 0.474 mmol) in ethyl acetate (4 mL) were added 5-chlorothiophene-2-sulfonyl chloride (0.206 g) and n,n-diisopropylethylamine (0.248 mL, 1.42 mmol). The reaction mixture was stirred for 1 h at room temperature, water was added and it was extracted with ethyl acetate. The combined organic layers were dried over $Na_2SO_4$ and evaporated to give a yellow gum which was purified by flash chromatography to give 5-chloro-N-[[1-(2-methoxyethyl)-4-methyl-2-oxo-4H-3,1-benzoxazin-6-yl]methyl]thiophene-2-sulfonamide (58 mg, 28%) of a colourless gum.

LCMS: 0.91 min; ES+ 431/433 (M+H+); 1H NMR (400 MHz, CHLOROFORM-d) 7.42 (d, 1H), 7.23 (dd, 1H), 7.14 (d, 1H), 7.03 (d, 1H), 6.96 (d, 1H), 5.35 (q, 1H), 4.84 (t, 1H), 4.24 (d, 2H), 4.15-4.04 (m, 2H), 3.73 (t, 2H), 3.38 (s, 3H), 1.68 (d, 3H).

Further compounds of the present invention were made using the same methods, as shown in Table 2 below.

TABLE 2

Additional compounds synthesised

| Compound | Name | RT (min) | [M + H] (measured) |
|---|---|---|---|
| 13.001 | N-[(1-ethyl-4-methyl-2-oxo-4H-3,1-benzoxazin-6-yl)methyl]-benzenesulfonamide | 0.87 | 361 |
| 13.006 | N-[(1-ethyl-4-methyl-2-oxo-4H-3,1-benzoxazin-6-yl)methyl]-2,4-difluoro-benzenesulfonamide | 0.89 | 397 |
| 14.012 | 4-methyl-N-[(4-methyl-2-oxo-1-propyl-4H-3,1-benzoxazin-6-yl)methyl]benzenesulfonamide | 0.97 | 389 |
| 14.006 | N-[(4-methyl-2-oxo-1-propyl-4H-3,1-benzoxazin-6-yl)methyl]-2,4-difluoro-benzenesulfonamide | 0.94 | 411 |
| 14.001 | N-[(4-methyl-2-oxo-1-propyl-4H-3,1-benzoxazin-6-yl)methyl]-benzenesulfonamide | 0.92 | 375 |
| 30.001 | N-[[8-fluoro-1-(3-fluoropropyl)-4-methyl-2-oxo-4H-3,1-benzoxazin-6-yl]methyl]benzenesulfonamide | 0.89 | 411 |
| 29.001 | N-[[8-fluoro-1-(2-methoxyethyl)-4-methyl-2-oxo-4H-3,1-benzoxazin-6-yl]methyl]benzenesulfonamide | 0.88 | 409 |
| 26.048 | 5-chloro-N-[[1-(2-methoxyethyl)-4-methyl-2-oxo-4H-3,1-benzoxazin-6-yl]methyl]thiophene-2-sulfonamide | 0.91 | 431/433 |
| 28.048 | 5-chloro-N-[[1-(2,2-difluoroethyl)-4-methyl-2-oxo-4H-3,1-benzoxazin-6-yl]methyl]thiophene-2-sulfonamide | 0.98 | 437/439 |
| 18.048 | 5-chloro-N-[[4-methyl-2-oxo-1-(2,2,2-trifluoroethyl)-4H-3,1-benzoxazin-6-yl]methyl]thiophene-2-sulfonamide | 0.98 | 455/457 |
| 24.048 | 5-chloro-N-[[1-(cyclopropylmethyl)-4-methyl-2-oxo-4H-3,1-benzoxazin-6-yl]methyl]thiophene-2-sulfonamide | 0.99 | 427/429 |
| 24.009 | N-[[1-(cyclopropylmethyl)-4-methyl-2-oxo-4H-3,1-benzoxazin-6-yl]methyl]-4-fluoro-benzenesulfonamide | 0.93 | 405 |
| 28.009 | N-[[1-(2,2-difluoroethyl)-4-methyl-2-oxo-4H-3,1-benzoxazin-6-yl]methyl]-4-fluoro-benzenesulfonamide | 0.88 | 415 |
| 18.009 | 4-fluoro-N-[[4-methyl-2-oxo-1-(2,2,2-trifluoroethyl)-4H-3,1-benzoxazin-6-yl]methyl]benzenesulfonamide | 0.92 | 433 |
| 26.009 | 4-fluoro-N-[[1-(2-methoxyethyl)-4-methyl-2-oxo-4H-3,1-benzoxazin-6-yl]methyl]benzenesulfonamide | 0.84 | 408 |
| 28.001 | N-[[1-(2,2-difluoroethyl)-4-methyl-2-oxo-4H-3,1-benzoxazin-6-yl]methyl]benzenesulfonamide | 0.86 | 397 |
| 27.001 | N-[[1-(3-fluoropropyl)-4-methyl-2-oxo-4H-3,1-benzoxazin-6-yl]methyl]benzenesulfonamide | 0.87 | 393 |
| 24.001 | N-[[1-(cyclopropylmethyl)-4-methyl-2-oxo-4H-3,1-benzoxazin-6-yl]methyl]benzenesulfonamide | 0.92 | 387 |
| 18.001 | N-[[4-methyl-2-oxo-1-(2,2,2-trifluoroethyl)-4H-3,1-benzoxazin-6-yl]methyl]benzenesulfonamide | 0.91 | 415 |
| 26.001 | N-[[1-(2-methoxyethyl)-4-methyl-2-oxo-4H-3,1-benzoxazin-6-yl]methyl]benzenesulfonamide | 0.83 | 391 |
| 20.001 | N-[(1-ethyl-8-fluoro-4-methyl-2-oxo-4H-3,1-benzoxazin-6-yl)methyl]benzenesulfonamide | 0.90 | 379 |
| 25.001 | N-[(8-fluoro-4-methyl-2-oxo-1-propyl-4H-3,1-benzoxazin-6-yl)methyl]benzenesulfonamide | 0.95 | 393 |
| 14.048 | 5-chloro-N-[(4-methyl-2-oxo-1-propyl-4H-3,1-benzoxazin-6-yl)methyl]thiophene-2-sulfonamide | 1.00 | 415/417 |
| 13.048 | 5-chloro-N-[(1-ethyl-4-methyl-2-oxo-4H-3,1-benzoxazin-6-yl)methyl]thiophene-2-sulfonamide | 0.94 | 401/403 |

LCMS—Method

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Biological Examples

A) Reduced Plant Water Use in Corn

Compounds were tested for their effect on reducing plant water use as follows. The compounds were applied by foliar spray to 12 day old corn plants (variety NK OCTET) grown in controlled environment plant growth chambers. All compounds were applied using an emulsifiable concentrate (EC) formulation that was diluted to the desired concentrations with water containing 0.4% of the adjuvant rape seed methyl ester. Plant water use during the day was assessed by repeated weighing of the pots in which the plants were grown before and after application of the compounds at the indicated times (expressed in days after application (DAA)). The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

Application of the chemicals (0 DAA) took place approximately between 08:00 and 09:30 a.m. Water use (WU) was measured within day time (chamber light is on 06:00 to 20:00) at these timepoints: 0 DAA a.m. (10:30-12:50), 0 DAA p.m. (14:00-19:50).

TABLE A1

Percent increase or decrease of water use (WU) during day time of corn plants sprayed with the indicated compounds at 500 µM compared to a negative control treatment (e.g. 0 = identical to negative control; −8.5 = −8.5% decrease in water use compared to negative control treatment). Average WU values of 6 pots (each with three plants) per treatment are shown.

| | % WU | |
|---|---|---|
| Compound | 0 DAA (AM) | 0DAA (PM) |
| Untreated Control | 0 | 0 |
| 3.001 | −12% | −7% |

A further trial was conducted to test further compounds of the present invention using the same protocol.

TABLE A2

Percent increase or decrease of water use (WU) during day time of corn plants sprayed with the indicated compounds at 500 µM compared to a negative control treatment (e.g. 0 = identical to negative control; −8.5 = −8.5% decrease in water use compared to negative control treatment). Average WU values of 6 pots (each with three plants) per treatment are shown.

| | % WU | |
|---|---|---|
| Compound | 0 DAA (AM) | 0DAA (PM) |
| Untreated Control | 0 | 0 |
| 26.048 | −17 | −12 |
| 28.048 | −33 | −39 |
| 18.048 | −25 | −27 |
| 24.048 | −40 | −47 |
| 24.009 | −18 | −13 |
| 18.009 | −18 | −14 |
| 26.009 | −47 | −46 |
| 28.001 | −27 | −31 |
| 27.001 | −50 | −58 |
| 24.001 | −29 | −27 |
| 18.001 | −19 | −16 |
| 26.001 | −25 | −20 |
| 20.001 | −37 | −42 |
| 25.001 | −48 | −56 |
| 14.001 | −48 | −52 |
| 14.006 | −34 | −37 |
| 14.012 | −36 | −40 |
| 14.048 | −54 | −57 |
| 13.048 | −48 | −51 |
| 13.001 | −38 | −40 |
| 13.006 | −24 | −21 |

The results show that corn plants treated with compounds of the present invention use less water than untreated plants.

A further trial was conducted to compare the water use of a compound of the present invention with a corresponding compound where Y is not a heteroatom.

TABLE A3

Percent increase or decrease of water use (WU) during day time of corn plants sprayed with the indicated compounds at 500 µM compared to a negative control treatment (e.g. 0 = identical to negative control; −8.5 = −8.5% decrease in water use compared to negative control treatment). Average WU values of 6 pots (each with three plants) per treatment are shown.

| | % WU | |
|---|---|---|
| Compounds | 0 DAA (AM) | 0 DAA (PM) |
| Untreated Control | 0 | 0 |
| Compound A | −25 | −24 |
| Compound 13.001 | −38 | −40 |

This data shows that compound 13.001 is a more potent ABA agonist than dihydroquinolinone compound A, which is the corresponding compound without a heteroatom.

B) Reduced Plant Water Use in Soybean

Compounds were tested for their effect on reducing plant water use as follows. The compounds were applied by foliar spray to 12 day old soybean plants (variety S20-G7) grown in controlled environment plant growth chambers. All compounds were applied using an emulsifiable concentrate (EC) formulation that was diluted to the desired concentration with water containing additional surfactant (EXTRAVON 1 g/20 L). Plant water use during the day was assessed by repeated weighing of the pots in which the plants were grown before and after application of the compounds at the indicated times (expressed in days after application (DAA)). The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

Application of the chemicals (0 DAA) took place approximately between 08:00 and 09:30 a.m. Water use (WU) was measured within day time (chamber light is on 06:00 to 20:00) at these timepoints: 0 DAA a.m. (10:30-12:50), 0 DAA p.m. (14:00-19:50).

TABLE A4

Percent increase or decrease of water use (WU) during day time of soybean plants sprayed with the indicated compounds at 125 µM compared to a negative control treatment (e.g. 0 = identical to negative control; −8.5 = −8.5% decrease in water use compared to negative control treatment). Average WU values of 6 pots (each with three plants) per treatment are shown.

| Compounds | % WU | |
|---|---|---|
| | 0 DAA (AM) | 0 DAA (PM) |
| Untreated control | 0 | 0 |
| 14.048 | −51 | −55 |
| 14.001 | −49 | −55 |
| 25.001 | −48 | −53 |

The results show that soybean plants treated with compounds of the present invention use less water than untreated plants.

The invention claimed is:

1. A compound of formula (I)

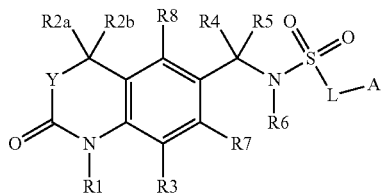

(I)

wherein:

R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$ alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;

R2a and R2b are independently selected from the group consisting of hydrogen, $C_1$-$C_4$ alkyl and $C_1$-$C_4$ haloalkyl; or R2a and R2b, together with the atom to which they are attached, are joined to form a $C_3$-$C_6$ cycloalkyl;

R3, R7 and R8 are independently selected from the group consisting of hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl;

R4 and R5 are independently selected from the group consisting of hydrogen, $C_1$-$C_4$ alkyl, $C_1$-$C_4$ haloalkyl and $C_3$-$C_4$ cycloalkyl;

or R4 and R5 together with the atom to which they are attached, are joined to form a $C_3$-$C_4$ cycloalkyl or $C_4$ heterocyclyl;

R6 is selected from the group consisting of hydrogen, $C_1$-$C_4$ alkyl, $C_3$-$C_4$ alkenyl, $C_3$-$C_4$ alkynyl, and $C_1$-$C_3$ alkoxy-$C_1$-$C_4$-alkyl;

L is selected from the group consisting of a bond, a linear —$C_1$-$C_4$— alkyl chain, a linear —$C_2$-$C_4$— alkenyl chain, a linear —$C_2$-$C_4$— alkynyl chain, a linear —$C_1$-$C_4$— alkoxy chain whereby the oxygen atom is attached to A, a linear -amino—$C_1$-$C_4$—alkyl- chain whereby the nitrogen atom is attached to A, and a linear $C_1$-$C_2$alkyl-oxy-$C_1$-$C_2$alkyl, chain each optionally substituted with one to three halogen, cyano, $C_1$-$C_4$ alkyl, $C_1$-$C_4$ haloalkyl or $C_1$-$C_4$ alkoxy;

A is selected from the group consisting of hydrogen, $C_1$-$C_7$ alkyl, $C_3$-$C_5$ cycloalkyl, 3-10 membered heterocyclyl and aryl, each optionally substituted with one to three Ry;

Y is selected from the group consisting of O and NRw;

Rw is selected from the group consisting of hydrogen, $C_1$-$C_4$ alkyl, $C_1$-$C_4$ alkoxy, $C_1$-$C_4$ alkoxycarbonyl, $C_1$-$C_4$ haloalkyl, $C_3$-$C_4$ alkenyl, and $C_3$-$C_4$ alkynyl;

each Rx is, independently of the other, selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;

each Ry is, independently of the other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl which cycloalkyl is unsubstituted or substituted by one or more Rz;

each Rz is, independently of the other, selected from the group consisting of halogen, $C_1$-$C_4$-alkyl and $C_1$-$C_4$-haloalkyl;

wherein A is not butyl when either R4 or R5 is methyl;
and wherein R1 is not methyl when R2, R3, R4, R5, R6, R7 and R8 are each hydrogen;
or salts or N-oxides thereof.

2. A compound according to claim 1, wherein R1 is selected from the group consisting of $C_1$-$C_6$ alkyl, $C_1$-$C_6$ haloalkyl, $C_3$-$C_6$ alkenyl and $C_3$-$C_5$ cyclopropyl-$C_1$-$C_6$-alkyl, each optionally substituted with one to three Rx.

3. A compound according to claim 2, wherein R1 is ethyl or propyl.

4. A compound according to claim 1, wherein L is a bond.

5. A compound according to claim 1, wherein A is selected from the group consisting of $C_1$-$C_7$ alkyl, phenyl and 3-6 membered heteroaryl, each optionally substituted with one to three Ry.

6. A compound according to claim 5, wherein A is phenyl optionally substituted with one to three substituents independently selected from the group consisting of halogen, $C_1$-$C_4$ haloalkyl, $C_1$-$C_4$ alkyl and $C_1$-$C_4$ haloalkoxy.

7. A compound according to claim 1, wherein Y is O.

8. A compound according to claim 1, wherein R2a and R2b are independently selected from the group consisting of hydrogen and $C_1$-$C_4$ alkyl.

9. A compound according to claim 1, wherein R3 is selected from the group consisting of hydrogen, halogen and $C_1$-$C_4$ alkyl.

10. A compound according to claim 1, wherein R2a is methyl, and R2b, R3, R4, R5, R6, R7 and R8 are hydrogen.

11. A composition comprising a compound according to claim 1, and an agriculturally acceptable formulation adjuvant.

12. A mixture comprising a compound as defined in claim 1, and an active ingredient.

13. A crop yield enhancing composition, comprising a compound according to claim 1.

14. A crop yield enhancing composition, comprising a composition according to claim 11.

15. A crop yield enhancing composition, comprising a mixture according to claim 12.

16. A method for improving the tolerance of a plant to abiotic stress, regulating or improving the growth of a plant, or improving the yield of a plant, wherein the method comprises applying to the plant, plant part, plant propagation material, or plant growing locus a compound according to claim 1.

17. A method for improving the tolerance of a plant to abiotic stress, regulating or improving the growth of a plant, or improving the yield of a plant, wherein the method comprises applying to the plant, plant part, plant propagation material, or plant growing locus a composition according to claim 11.

18. A method for improving the tolerance of a plant to abiotic stress, regulating or improving the growth of a plant, or improving the yield of a plant, wherein the method comprises applying to the plant, plant part, plant propagation material, or plant growing locus a mixture according to claim 12.

19. A method for inhibiting seed germination of a plant, wherein the method comprises applying to the plant, plant part, plant propagation material or plant growing locus a compound according to claim 1.

20. A method for inhibiting seed germination of a plant, wherein the method comprises applying to the plant, plant part, plant propagation material or plant growing locus a composition according to claim 11.

21. A method for inhibiting seed germination of a plant, wherein the method comprises applying to the plant, plant part, plant propagation material or plant growing locus a mixture according to claim 12.

* * * * *